United States Patent
Chappell, III et al.

(10) Patent No.: US 11,303,976 B2
(45) Date of Patent: Apr. 12, 2022

(54) PRODUCTION AND CONTROL OF CINEMATIC CONTENT RESPONSIVE TO USER EMOTIONAL STATE

(71) Applicant: WARNER BROS. ENTERTAINMENT INC., Burbank, CA (US)

(72) Inventors: Arvel A. Chappell, III, Los Angeles, CA (US); Lewis S. Ostrover, Los Angeles, CA (US)

(73) Assignee: WARNER BROS. ENTERTAINMENT INC., Burbank, CA (US)

( * ) Notice: Subject to any disclaimer, the term of this patent is extended or adjusted under 35 U.S.C. 154(b) by 0 days.

(21) Appl. No.: 16/833,492

(22) Filed: Mar. 27, 2020

(65) Prior Publication Data

US 2020/0296480 A1 Sep. 17, 2020

Related U.S. Application Data

(63) Continuation of application No. PCT/US2018/053218, filed on Sep. 27, 2018.
(Continued)

(51) Int. Cl.
*H04H 60/33* (2008.01)
*H04H 60/56* (2008.01)
(Continued)

(52) U.S. Cl.
CPC ......... *H04N 21/8545* (2013.01); *A61B 5/163* (2017.08); *A61B 5/165* (2013.01);
(Continued)

(58) Field of Classification Search
CPC ......... H04N 21/8545; H04N 21/42201; H04N 21/44218; H04N 21/4532; H04N 21/4667;
(Continued)

(56) References Cited

U.S. PATENT DOCUMENTS 4,305,131 A 12/1981 Best
8,069,125 B2 11/2011 Jung et al.
(Continued)

FOREIGN PATENT DOCUMENTS

WO    WO 2016/172557 A1    10/2016

OTHER PUBLICATIONS

WO PCT/US2018/053218 ISR and Written Opinion dated Jan. 17, 2019.
(Continued)

*Primary Examiner* — Kyu Chae
(74) *Attorney, Agent, or Firm* — One LLP

(57) ABSTRACT

A computer-implemented method for providing cinematic content to a user via a computer-controlled media player includes accessing by a processor a content package including a targeted emotional arc and a collection of digital objects each associated with codes indicating an emotional profile of the each digital object, playing digital objects selected from the content package thereby outputting an audio-video signal for display by an output device; receiving sensor data from at least one sensor positioned to sense a biometric feature of a user watching the output device; determining a value of one or more emotional state variables, based on the sensor data; and selecting the digital objects for the playing based on the one or more emotional state variables, a recent value of the targeted emotional arc, and the one or more codes indicating an emotional profile. An apparatus is configured to perform the method using hardware, firmware, and/or software.

19 Claims, 19 Drawing Sheets

Related U.S. Application Data

(60) Provisional application No. 62/715,766, filed on Aug. 7, 2018, provisional application No. 62/661,556, filed on Apr. 23, 2018, provisional application No. 62/614,811, filed on Jan. 8, 2018, provisional application No. 62/566,257, filed on Sep. 29, 2017.

(51) Int. Cl.

| | | |
|---|---|---|
| *H04N 7/10* | (2006.01) | |
| *H04N 7/025* | (2006.01) | |
| *H04N 21/8545* | (2011.01) | |
| *H04N 21/422* | (2011.01) | |
| *H04N 21/45* | (2011.01) | |
| *H04N 21/8541* | (2011.01) | |
| *H04N 21/442* | (2011.01) | |
| *H04N 21/466* | (2011.01) | |
| *A61B 5/16* | (2006.01) | |
| *G16H 40/67* | (2018.01) | |
| *G16H 50/20* | (2018.01) | |
| *G06F 3/01* | (2006.01) | |
| *G09B 19/00* | (2006.01) | |

(52) U.S. Cl.
CPC .............. *G06F 3/011* (2013.01); *G09B 19/00* (2013.01); *G16H 40/67* (2018.01); *G16H 50/20* (2018.01); *H04N 21/42201* (2013.01); *H04N 21/44218* (2013.01); *H04N 21/4532* (2013.01); *H04N 21/4667* (2013.01); *H04N 21/8541* (2013.01)

(58) Field of Classification Search
CPC .... H04N 21/8541; A61B 5/163; A61B 5/165; G16H 40/67; G16H 50/20; G06F 3/011; G09B 19/00
See application file for complete search history.

(56) References Cited

U.S. PATENT DOCUMENTS

| | | |
|---|---|---|
| 9,736,603 B2 | 8/2017 | Osborne et al. |
| 10,025,972 B2 | 7/2018 | Matas et al. |
| 2002/0073417 A1 | 6/2002 | Kondo et al. |
| 2007/0168315 A1 | 7/2007 | Covannon et al. |
| 2008/0161109 A1 | 7/2008 | Chainer et al. |
| 2010/0211439 A1 | 8/2010 | Marci et al. |
| 2011/0169603 A1 | 7/2011 | Fithian et al. |
| 2011/0320536 A1 | 12/2011 | Lobb et al. |
| 2012/0324492 A1 | 12/2012 | Treadwell, III et al. |
| 2013/0046577 A1 | 2/2013 | Marci et al. |
| 2013/0232515 A1 | 9/2013 | Rivera et al. |
| 2013/0280682 A1 | 10/2013 | Levine et al. |
| 2013/0283162 A1* | 10/2013 | Aronsson ......... H04N 21/42201 715/719 |
| 2014/0130076 A1 | 5/2014 | Moore et al. |
| 2014/0150002 A1 | 5/2014 | Hough et al. |
| 2014/0221866 A1 | 8/2014 | Quy |
| 2014/0270683 A1 | 9/2014 | Zhu et al. |
| 2014/0350349 A1 | 11/2014 | Geurts et al. |
| 2015/0093729 A1 | 4/2015 | Plans et al. |
| 2015/0127737 A1 | 5/2015 | Thompson et al. |
| 2015/0142553 A1 | 5/2015 | Kodra et al. |
| 2015/0181291 A1* | 6/2015 | Wheatley ............... H04N 21/84 725/10 |
| 2015/0193089 A1 | 7/2015 | Berlin et al. |
| 2016/0077547 A1 | 3/2016 | Aimone et al. |
| 2016/0191893 A1 | 6/2016 | Gewickey et al. |
| 2016/0228744 A1 | 8/2016 | Szacherski |
| 2017/0055033 A1 | 2/2017 | Christie |
| 2017/0123824 A1 | 5/2017 | Franck |
| 2017/0147202 A1 | 5/2017 | Donohue |
| 2017/0169727 A1 | 6/2017 | Briggs et al. |
| 2017/0171614 A1 | 6/2017 | Kalliouby et al. |
| 2017/0243055 A1 | 8/2017 | Naveh |
| 2017/0251262 A1 | 8/2017 | Bist et al. |
| 2018/0376187 A1* | 12/2018 | Everett ............ H04N 21/25883 |
| 2019/0297380 A1 | 9/2019 | Dominguez et al. |
| 2020/0060598 A1 | 2/2020 | Palti-Wasserman |
| 2020/0134084 A1 | 4/2020 | Rakshit et al. |
| 2020/0267451 A1 | 8/2020 | Pudhiyaveetil et al. |
| 2020/0296458 A1 | 9/2020 | Chappell, III et al. |
| 2020/0297262 A1 | 9/2020 | Chappell, III et al. |
| 2020/0405212 A1 | 12/2020 | Chappell, III et al. |
| 2020/0405213 A1 | 12/2020 | Chappell, III et al. |
| 2021/0056407 A1 | 2/2021 | Buesser et al. |

OTHER PUBLICATIONS

"#613: Storytelling in VR from a Depth Psychological & Mythological Perspective", 2018, retrieved from https://voicesofvr.com/613-storytelling-in-vr-from-a-depth-psychological-mythological-perspective/, pp. 1-4.

"Ad firms using tools to help them read your mind", 2017, retrieved from https://technology.inquirer.net/70804/ad-firms-using-tools-help-read-mind, pp. 1-7.

Bound, K., "AI: discover how viewer emotions guide the narrative direction of a movie", 2018, retrieved from https://www.linkedin.com/pulse/ai-how-viewer-emotions-guide-narrative-direction-keith, pp. 1-5.

Breland, A., "Facebook patents technology that would estimate users' socioeconomic status", 2018, retrieved from https://thehill.com/policy/technology/372017-facebook-patents-tech-to-estimate-users-socioeconomic-status, pp. 1-2.

Castellanos, S., "Siri Contributor Tackles Software That Detects Emotional States", 2018, retrieved from https://www.wsj.com/articles/siri-contributor-tackles-software-that-detects-emotional-states-1520548561, pp. 1-2.

Chan, S., "Interaxon measures brainwaves to give VR devs more data for game design", 2018, retrieved from https://venturebeat.com/2018/01/13/interaxon-measures-brainwaves-to-give-vr-devs-more-data-for-game-design/, pp. 1-6.

Coldeway, D., "This facial recognition system tracks how you're enjoying a movie", 2017, retrieved from https://techcrunch.com/2017/07/25/this-facial-recognition-system-tracks-how-youre-enjoying-a-movie/, pp. 1-2.

Crooke, J., "Uber applies for patent that would protect drunk passengers", 2018, retrieved from https://techcrunch.com/2018/06/11/uber-applies-for-patent-that-would-detect-drunk-passengers/, pp. 1-3.

Dormehl, L., "Frighteningly accurate 'mind reading' AI reads brain scans to guess what you're thinking", 2017, retrieved from https://www.digitaltrends.com/cool-tech/ai-predicts-what-youre-thinking/, pp. 1-8.

Dormehl, L., "New VR horror game gets scarier if your heart rate isn't fast enough", 218, retrieved from https://www.digitaltrends.com/cool-tech/bring-to-light-heart-rate-vr/, pp. 1-7.

Fadelli, I., "Researchers use machine learning to analyse movie preferences", 2018, retrieved from https://techxplore.com/news/2018-07-machine-analyse-movie.html, pp. 1-3.

Harman, A., "Ford Research Gives New Meaning to 'Rush Hour'", 2018, retrieved from https://www.wardsauto.com/industry/ford-research-gives-new-meaning-rush-hour, pp. 1-7.

Hasson, U., et al., "Neurocinematics: The Neuroscience of Film", Projections, 2008, vol. 2, No. 1, pp. 1-26.

Kaufman, D., "Nab 2018: Machine-Learning Tools to Become Vital for Editing", 2018, retrieved from https://www.etcentric.org/nab-2018-machine-learning-tools-to-beomce-vital-for-editing/), pp. 1-3.

Kaufman, D., "Nab 2018: Potential Impact of AI on Storytelling, Moviemaking", 2018, retrieved from https://www.etcentric.org/nab-2018-potentialimpact-of-ai-on-storytelling-moviemaking/, pp. 1-3.

Lefebvre, R., "MIT's wearable device can 'hear' the words you say in your head", 2018, retrieved from https://www.engadget.com/2018-04-06-mit-wearable-silent-words.html, pp. 1-7.

Marsella, S., et al., "Computational Models of Emotion", Draft Manuscript, pp. 1-30.

(56) References Cited

OTHER PUBLICATIONS

Parker, L., "Video Game Creators Seek Ouy Hollywood for Robust Narratives", 2017, retrieved from https://www.nytimes.com/2017/12/20/technology/video-game-creators-hollywood-writers.html#:~:text=When%20Pete%20Samuels%2C%20a%20founder,So%20he%20turned %20to%20Hollywood., pp. 1-4.

Riedl, M. O., et al., "From Linear Story Generation to Branching Story Graphs", IEEE Computer Graphics and Applications, 2006, pp. 23-31.

Siegel, T., "This New Artificial Intelligence Script-Reading Program Could Find Your Next Oscar Role (Exclusive)", 2016, retrieved from https://www.hollywoodreporter.com/news/general-news/new-artificial-intelligence-scri pt-reading-866554/, pp. 1-3.

Solsman, J.E., et al., "Oculus wants to make immersive virtual theater a reality", 2018, retrieved from https://www.cnet.com/tech/mobile/oculus-wants-to-make-immersive-virtual-theater-a-reality/, pp. 1-4.

Simonite, T., "This Call May Be Monitored for Tone and Emotion", 2018, retrieved from https://www.wired.com/story/this-call-may-be-monitored-for-tone-and-emotion/, pp. 1-8.

Trew, J., "Dolby knows what you're feeling at the movies", 2018, retrieved from https://www.engadget.com/2018-01-12-dolby-knows-what-youre-watching-based-on-your-b.html, pp. 1-5.

"Turning Design Mockups Into Code With Deep Learning", 2018, retrieved from https://blog.floydhub.com/turning-design-mockups-into-code-with-deep-learning/, pp. 1-41.

Waltz, E., "A New Wearable Brain Scanner", 2018, retrieved from https://spectrum.IEEE.org/the-human-os/biomedical/imaging/a-new-wearable-brain-scanner, pp. 1-4.

Wang, J., et al., "Predicting the Brain Activation Pattern Associated With the Propositional Content of a Sentence: Modeling Neural Representations of Events and States", Human Brain Mapping, 2017, vol. 38, No. 10, pp. 4865-4881.

Webb, A., "Apple Is Developing an EKG Heart Monitor for Its Smartwatch", 2017, retrieved from https://www.bloomberg.com/news/articles/2017-12-21/apple-is-said-to-develop-ekg-heart-monitor-for-future-watch, pp. 1-2.

"Aside", 2016, retrieved from https://web.archive.org/web/20161117103448/htpps://en.wikipedia.org/wiki/Aside, 2 pages.

Turk, V., "Shakespeare, Remixed by Biosensors", 2014, retrieved from https://www.vice.com/en/article/bmjmd8/shakespeare-remixed-by-biosensors, 7 pages.

PCT/US2018/053625 ISR and Written Opinion dated Dec. 27, 2018.

PCT/US2018/053614 ISR and Written Opinion dated Jan. 17, 2019.

PCT/US2019/012567 ISR and Written Opinion dated Apr. 11, 2019.

PCT/US2019/012783 ISR and Written Opinion dated Apr. 25, 2019.

Grant, C., "Many Worlds: The movie that watches its audience", BBQ News, retrieved from https://www.bbc.com/news/technology-21429437, 2013, pp. 1-5.

Kapur, A., et al., "AlterEgo: A Personalized Wearable Silent Speech Interface", IUI '18: 23rd International Conference on Intelligent User Interfaces, Mar. 2018, Tokyo, Japan, pp. 43-53.

EP 18861951.4 Extended Search Report dated Aug. 9, 2021.

EP 19735809.6 Partial Supplementary Search Report, dated Nov. 4, 2021.

Gilroy, S.W., et al., "Exploring Passive User Interaction for Adaptive Narratives", Proceedings of the 2012 ACM international conference on Intelligent User Interfaces, 2012, Session: Designing Narratives & Theater, Lisbon, Portugal, pp. 119-128.

Katti, H., et al., "Affective video summarization and story board generation using Pupillary dilation and Eye gaze", 2011 IEEE International Symposium on Multimedia, 2011, Dana Point, CA, pp. 319-326.

Sourina, O., et al., "EEG-Based Personalized Digital Experience", International Conference on Universal Access in Human-Computer Interaction, 2011, pp. 591-599.

EP 19736258.5, Supplementary Search Report, dated Oct. 26, 2021.

\* cited by examiner

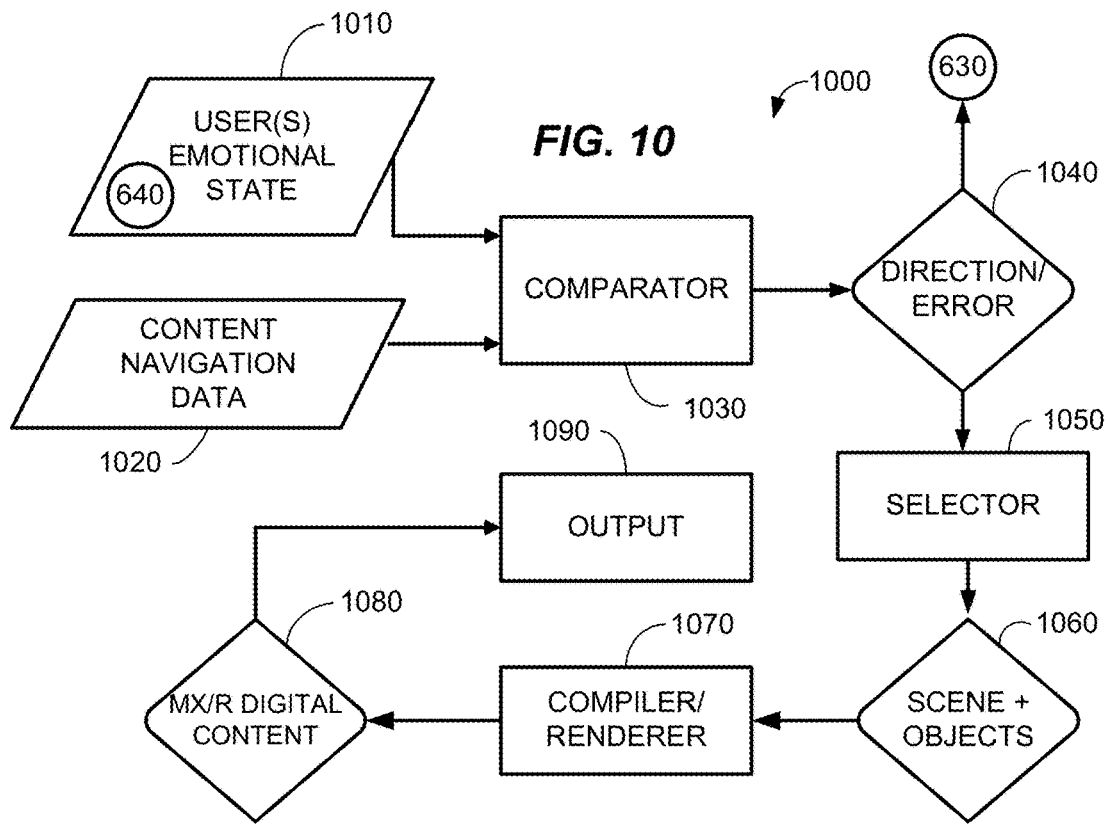
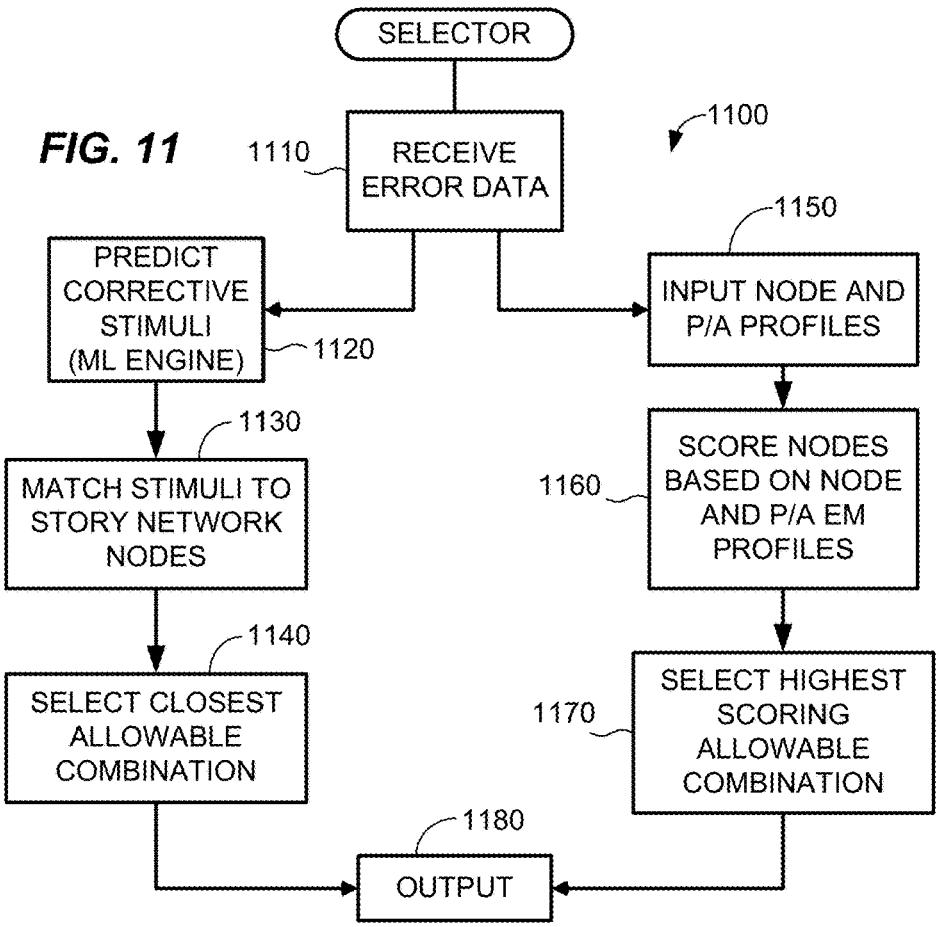

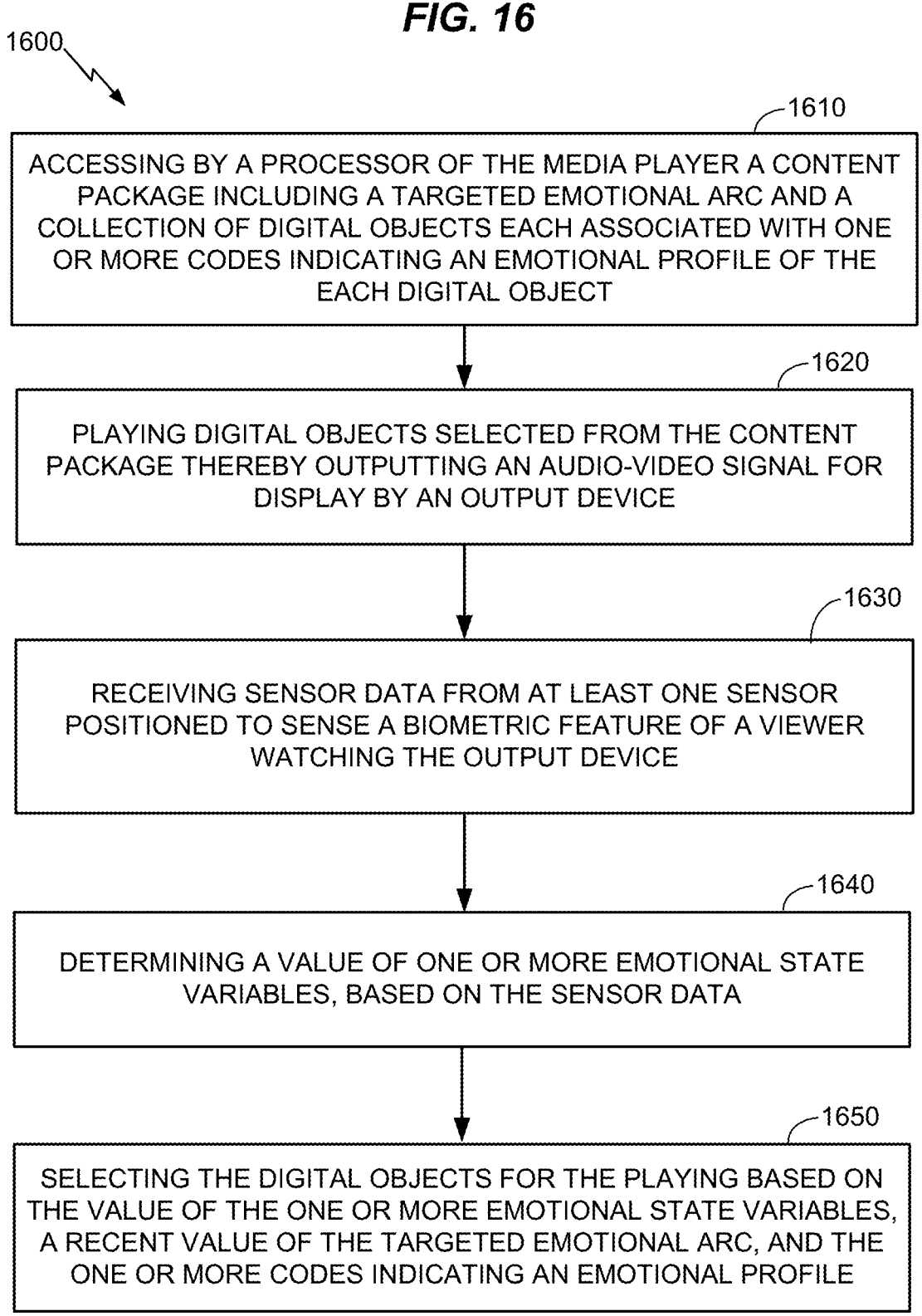

PRODUCTION AND CONTROL OF CINEMATIC CONTENT RESPONSIVE TO USER EMOTIONAL STATE

CROSS-REFERENCE TO RELATED APPLICATION

The present application is a continuation of International (PCT) patent application No. PCT/US18/53218 filed Sep. 27, 2018, which claims priority to U.S. provisional patent application Ser. No. 62/715,766 filed Aug. 7, 2018, Ser. No. 62/661,556 filed Apr. 23, 2018, Ser. No. 62/614,811 filed Jan. 8, 2018, and Ser. No. 62/566,257 filed Sep. 29, 2017, the disclosures of all of which are incorporated herein in their entireties by reference.

FIELD

The present disclosure relates to methods and apparatus for producing and controlling digital cinematic content, a non-player character's interaction with users, or both, responsive to sensor data indicating a user's emotional state.

BACKGROUND

Branching narratives in computer-generated audio-video entertainment date back to the 1980's or earlier. Sophisticated video games of the present day blur the boundary between narrative and interactive entertainment, blending branching and interactive techniques. Immersive entertainment technologies such as virtual and augmented reality bring further opportunities to enthrall viewers. Data mining by machine learning enables discovery of new correspondences between low-level data and various targets, including consumer preferences and propensities. Proliferation of mobile phones and Internet of Things (IoT) devices drive an explosion of network-connected sensors. It is now possible to gather more real-time and batch data about consumers of content than ever before.

While new entertainment mediums and ever more spectacular effects entertain viewers as never before, the foundation for cinematic content remains the story and the actor. Successful movies combine compelling stories with convincing actors and visually and acoustically appealing arrangements usually aimed at the broadest possible audience for a film's genre. But movies are not made to be interactive. Production decisions are based on the director's artistic and business sensibilities often formed years or months prior to initial release. Large production budgets are spent on a fixed product that most viewers will see only once. The product is the same for everybody, all the time. Directors cannot possibly deliver a product that everyone will empathize with, so they create for a common denominator or market niche. Present cinematic offerings do not take advantage of available technology to deliver more interesting and compelling content for diverse viewers within a single content package.

It would be desirable, therefore, to develop new methods and other new technologies for production and control of cinematic content, that overcome these and other limitations of the prior art and deliver more compelling entertainment experiences for the audiences of tomorrow.

SUMMARY

This summary and the following detailed description should be interpreted as complementary parts of an integrated disclosure, which parts may include redundant subject matter and/or supplemental subject matter. An omission in either section does not indicate priority or relative importance of any element described in the integrated application. Differences between the sections may include supplemental disclosures of alternative embodiments, additional details, or alternative descriptions of identical embodiments using different terminology, as should be apparent from the respective disclosures.

In an aspect of the disclosure, a computer-implemented method for providing cinematic content to a user via a computer-controlled media player may include accessing by a processor of the media player a content package including a targeted emotional arc and a collection of digital objects each associated with one or more codes indicating an emotional profile of the each digital object, and playing digital objects selected from the content package thereby outputting an audio-video signal for display by an output device. The method may further include receiving sensor data from at least one sensor positioned to sense a variable biometric feature of a user watching the output device that indicates the user's neurological state, determining a value of one or more emotional state variables, based on the sensor data, and selecting the digital objects for the playing based on the one or more emotional state variables, a recent value of the targeted emotional arc, and the one or more codes indicating an emotional profile.

In an aspect each of the digital objects may be further encoded with one or more codes indicating a node of a story network, the selecting operation may further comprise selecting the digital objects further based on the one or more codes indicating a position of the node in a story network. The story network may be, or may include, a set of nodes including the node. Each of the nodes except for first and last ones of the nodes may be uniquely associated with one or more acceptable antecedent nodes consisting of a first proper non-empty subset of the set of nodes, and with one or more acceptable subsequent nodes consisting of a second proper non-empty subset of the set of nodes excluding the first proper non-empty subset. The antecedent nodes and subsequent nodes of each of the nodes may indicate its position in the story network.

The story network may include separate layers of story nodes, and the selecting may further include selecting digital objects each indicating a node from different ones of the separate layers for combining in a scene of the cinematic content. In an aspect, the playing may include combining story nodes from the separate layers of story nodes forming a combination. In another aspect, the selecting further may include selecting the digital objects indicating coinciding nodes of the separate layers. In an aspect, at least some of the set of nodes are associated with one or more coinciding nodes in different ones of the separate layers. Story software may encode an 'embedded playback chain,' a look-up table (LUT), or other method to ensure that threading through the nodes on each level continues to be consonant with the user's feelings and/or explicit interactions, and that the story and/or non-player character behaviors or arcs adjust as needed seamlessly.

In another aspect, the playing may include rendering one or more video frames based on the combination. In an alternative, or in addition, the playing may include obtaining pre-rendered data and providing to an output device.

In an aspect, the selecting may further include comparing the value of the one or more emotional state variables with the recent value of the targeted emotional arc, and selecting the digital objects at least in part by association with an emotional profile that compensates for deficiencies measured in the comparing. The targeted emotional arc may be, or may include, a set of targeted emotional values each uniquely associated with a different interval of a continuous time sequence. The method may include automatically modifying the targeted emotional arc during the playing based on at least one of prior emotional response data for the user or a demographic profile of the user.

Emotional responses are usually unintentional. In another aspect, the selecting may be further based on data indicating an intentional interaction by the user in response to the playing. The intentional interaction may include, for example, one or more of: speech directed to a character appearing in the output, an intentional muscle movement sensed by a user interface device or sensor, or intentional brain activity sensed by an electrical sensor. The method may further include controlling action of a character or object appearing in the output based on the data indicating an intentional interaction by the user in response to the playing.

The foregoing method may be implemented in any suitable programmable computing apparatus, by provided program instructions in a non-transitory computer-readable medium that, when executed by a computer processor, cause the apparatus to perform the described operations. The processor may be local to the apparatus and user, located remotely, or may include a combination of local and remote processors. An apparatus may include a computer or set of connected computers that is used in cinematic production or for output of cinematic content to one or more users. A cinematic output device may include, for example, a personal computer, mobile phone, notepad computer, virtual reality device, or augmented reality device. Other elements of the apparatus may include, for example, an audio output device and a user input device, which participate in the execution of the method. An apparatus may include a virtual or augmented reality device, such as a headset or other display that reacts to movements of a user's head and other body parts. The apparatus may include biometric sensors that provide data used by a controller to control details of the cinematic content.

To the accomplishment of the foregoing and related ends, one or more examples comprise the features hereinafter fully described and particularly pointed out in the claims. The following description and the annexed drawings set forth in detail certain illustrative aspects and are indicative of but a few of the various ways in which the principles of the examples may be employed. Other advantages and novel features will become apparent from the following detailed description when considered in conjunction with the drawings and the disclosed examples, which encompass all such aspects and their equivalents.

BRIEF DESCRIPTION OF THE DRAWINGS

The features, nature, and advantages of the present disclosure will become more apparent from the detailed description set forth below when taken in conjunction with the drawings in which like reference characters identify like elements correspondingly throughout the specification and drawings.

FIG. 10 is a flow chart illustrating aspects of real-time scene selection in response to a user's (player actor's) emotional state or aggregate of emotional states for multiple users.

FIG. 11 is a flow chart illustrating an example of a selection algorithm for real-time scene or object selection in response to a user's emotional state.

FIG. 16 is a flow chart illustrating aspects of a method for controlling output of digital cinematic content responsive to sensor data indicating a user's emotional state.

DETAILED DESCRIPTION

Various aspects are now described with reference to the drawings. In the following description, for purposes of explanation, numerous specific details are set forth in order to provide a thorough understanding of one or more aspects. It may be evident, however, that the various aspects may be practiced without these specific details. In other instances, well-known structures and devices are shown in block diagram form to facilitate describing these aspects.

Figure 1:
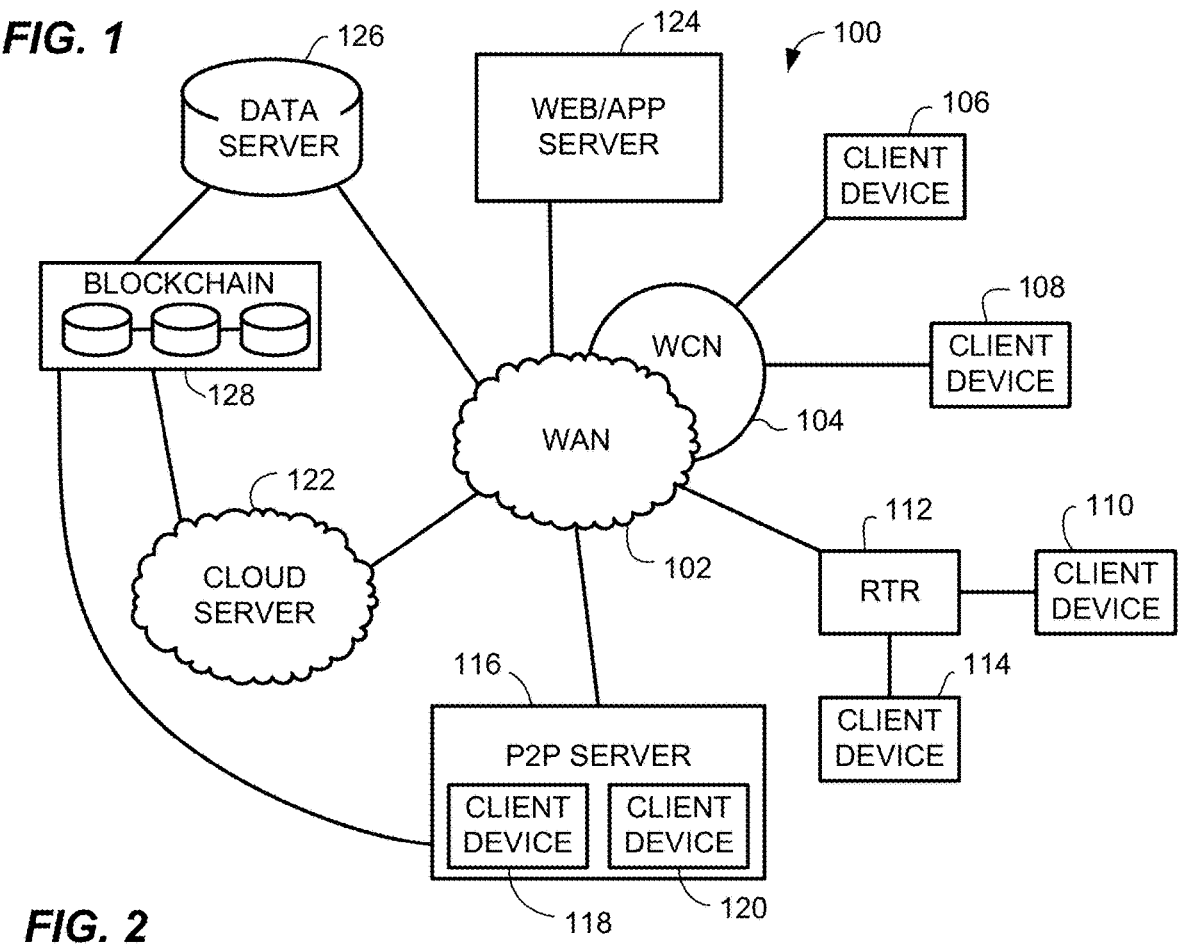
FIG. 1 is a schematic block diagram illustrating aspects of a system and apparatus for producing and controlling digital cinematic content responsive to sensor data indicating a user's emotional state, coupled to one or more distribution systems.

Referring to FIG. 1, methods for controlling output of digital cinematic content responsive to sensor data indicating a user's emotional state may be implemented in a client-server environment 100. Other architectures may also be suitable. In a network architecture, sensor data can be collected and processed locally, and used to control streaming data from a network source. In alternative embodiments, cinematic content may be controlled locally, and log data provided to a remote server for improving machine learning algorithms and tracking use. As used herein, "cinematic content" refers to digital audio-video content that is arranged at least in part by a script designed to entertain and evoke emotions in viewers according to a scheme for narrative tension, sometime referred to herein as an "emotional arc." The narrative tension planned by an emotional arc may cause the user to experience feelings of opposite polarity, e.g., fear and confidence or aversion and attraction at different times or in response to certain dramatic events, characters, objects, images, sounds, music, or other stimuli generated from the digital audio-video content. The intensity of these feelings often relates to the interest and pleasure the user gains from the experience and can also be planned by the emotional arc as tension builds, climaxes, and is relieved. Users of cinematic content naturally react during experience of the emotional arc by involuntarily entering neurological or neurophysiological states in tension (e.g., positive or negative emotions sometimes called valence, and intensity, amplitude or strength of the response, sometimes called arousal). In various embodiments, the cinematic content may be configured to support interactive features resembling video game features or may be devoid of interactive features except for responding to data indicative of user neurological or neurophysiological states.

If the content is configured to support it, users (also called "player actors") may also actively interact with characters or other objects appearing in the cinematic content. As used herein, a "player actor" is a user of a client device or interface equipped with or coupled to biometric sensors, who uses the client device or interface to interact with characters or objects in cinematic content by involuntarily entering a neurological or neurophysiological state (e.g., emoting), whether or not also using a controller to provide direct input, such that the narrative behavior of the character or object changes without requiring an intentional action by the player actor. "Narrative behavior" means behavior that changes the narrative, for example, character dialog or actions. Thus, player actors include users who affect the narrative by emoting inwardly or outwardly without taking an intentional action. The present description uses "user" and "player actor" interchangeably when discussing cinematic AI. Cinematic AI enables adaptation of the cinematic content to increase or maintain narrative tension experienced by the user, based on real time neurological feedback through biometric sensing of the user's involuntary neurological or neurophysiological states, e.g., valence and arousal.

A suitable client-server environment 100 may include various computer servers and client entities in communication via one or more networks, for example a Wide Area Network (WAN) 102 (e.g., the Internet) and/or a wireless communication network (WCN) 104, for example a cellular telephone network. Computer servers may be implemented in various architectures. For example, the environment 100 may include one or more Web/application servers 124 containing documents and application code compatible with World Wide Web protocols, including but not limited to HTML, XML, PHP and Javascript documents or executable scripts, for example. The environment 100 may include one or more data servers 126 for holding data, for example video, audio-video, audio, and graphical content components of cinematic content for consumption using a client device, software for execution on or in conjunction with client devices, for example sensor control and emotion detection applications, and data collected from users or client devices. Data collected from client devices or users may include, for example, sensor data and application data. Sensor data may be collected by a background (not user-facing) application operating on the client device, and transmitted to a data sink, for example, a cloud-based data server 122 or discrete data server 126. Application data means application state data, including but not limited to records of user interactions with an application or other application inputs, outputs or internal states. Applications may include software for control of cinematic content and supporting functions. Applications and data may be served from other types of servers, for example, any server accessing a distributed blockchain data structure 128, or a peer-to-peer (P2P) server 116 such as may be provided by a set of client devices 118, 120 operating contemporaneously as micro-servers or clients.

As used herein, users are always viewers of cinematic content from which a system node collects real-time emotional response data for use in controlling cinematic output. When actively participating in content via an avatar or other agency, users may also be referred to herein as player actors. Viewers are not always users. For example, a bystander may be a passive viewer that does not interact with the content via an emotional response. As used herein, a "node" includes a client or server participating in a computer network. As noted above, the present description also makes use of the term "player actor," to distinguish from prior interactive narratives in which the user is referred to as a "player character." Player characters interact with the narrative by manipulating a controller (e.g., keyboard or dedicated game controller) or other direct input. Unlike player actors, player characters cannot alter the narrative by achieving a biometric-detectable neurological state without any intentional action.

When interacting with cinematic AI by expression of emotion, the user is a player actor in the cinematic AI narrative. Player actors can interact with content in various ways, including for example natural language communication with NPCs and other player actors, locomotion and virtual locomotion within an immersive experience, and emotional feedback loop with other player actors, NPCs and the narrative environment.

The network environment 100 may include various client devices, for example a mobile smart phone client 106 and notepad client 108 connecting to servers via the WCN 104 and WAN 102; any one of the foregoing client devices, or a personal computer client device 110, a mixed reality (e.g., virtual reality or augmented reality) client device 114 connecting to servers via a router 112 and the WAN 102. In general, client devices may be, or may include, computers used by users to access cinematic content provided via a server or from local storage.

Figure 2:
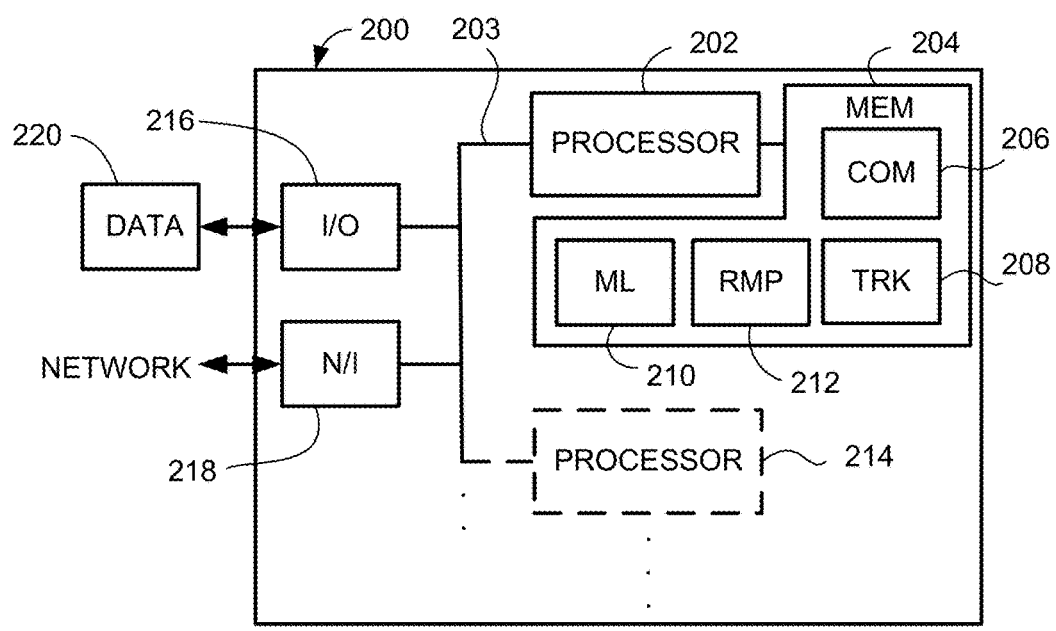
FIG. 2 is a schematic block diagram illustrating aspects of a server for producing digital cinematic content responsive to sensor data indicating a user's emotional state.

FIG. 2 shows a cinematic content server 200 for controlling output of digital cinematic content responsive to sensor data indicating a user's emotional state, which may operate in the environment 100, in similar networks, or as an independent server. The server 200 may include one or more hardware processors 202, 214 (two of one or more shown). Hardware includes firmware. Each of the one or more processors 202, 214 may be coupled to an input/output port 216 (for example, a Universal Serial Bus port or other serial or parallel port) to a source 220 for sensor data indicative of users' emotional states and viewing history. Viewing history may include a log-level record of variances from a baseline script for a content package or equivalent record of control decisions made in response to player actor emotional states and other input. Viewing history may also include content viewed on TV, Netflix and other sources. Any source that contains a derived emotional arc may be useful for input to an emotional-reacting content control algorithm. The server 200 may track player actor actions and emotional responses across multiple content titles for individuals or cohorts. Some types of servers, e.g., cloud servers, server farms, or P2P servers, may include multiple instances of discrete servers 200 that cooperate to perform functions of a single server.

The server 200 may include a network interface 218 for sending and receiving applications and data, including but not limited to sensor and application data used for controlling cinematic content. The content may be served from the server 200 to a client device or stored locally by the client device. If stored local to the client device, the client and server 200 may cooperate to handle sensor data and other player actor functions. In some embodiments, the client may handle all content control functions and the server 200 may be used for tracking only or may not be used at all. In other embodiments, the server 200 performs content control functions.

Each processor 202, 214 of the server 200 may be operatively coupled to at least one memory 204 holding functional modules 206, 208, 210, 212 of an application or applications for performing a method as described herein. The modules may include, for example, a communication module 206 for communicating with client devices and servers. The communication module 206 may include instructions that when executed by the processor 202 and/or 214 cause the server to communicate control data, content data, and sensor data with a client device via a network or other connection. A tracking module 208 may include functions for tracking emotional response and other interactive data for a user or cohort, for one or more content titles, subject to user permissions and privacy settings.

The modules may include, for example, a machine learning process (MLP) module 210. The MLP module 210 may include instructions that when executed by the processor 202 and/or 214 cause the server to perform one or more of applying a machine learning process encoded in a computer language to data indicative of player actor emotional reactions thereby identifying a user's internal state useful for a content control algorithm. The machine learning process 210 when executed by the processor may cause the server to assign a likelihood of a targeted outcome, e.g., a defined emotional state targeted for the cinematic content's emotional arc, for specific control actions.

The modules may further include a remote media player function 212 that when executed by the processor causes the server to perform any one or more of the functions described herein for a media player. In alternative embodiments, the remote media player function may be omitted from the server memory 204 and provided in the memory of a client device. The memory 204 may contain additional instructions, for example an operating system, and supporting modules.

Figure 3:
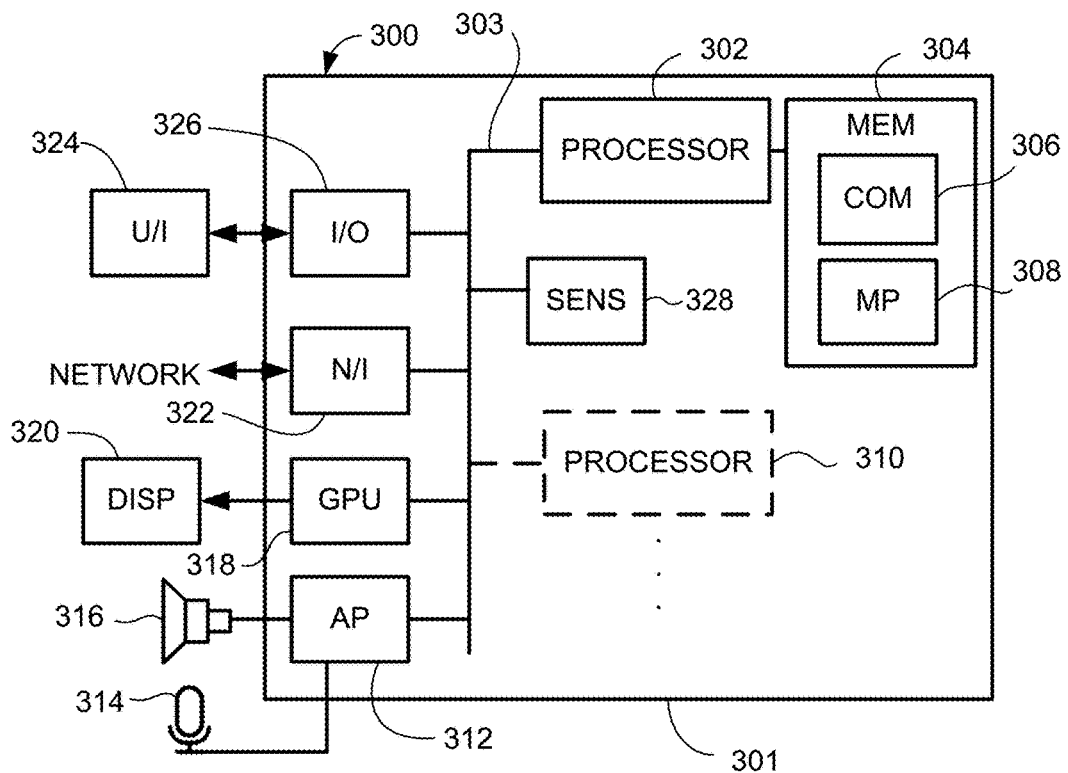
FIG. 3 is a schematic block diagram illustrating aspects of a client device for controlling output of digital cinematic content responsive to sensor data indicating a user's emotional state.

Referring to FIG. 3, aspects of a content consumption device 300 for controlling output of digital cinematic content responsive to sensor data indicating a user's emotional state. The apparatus 300 may include, for example, a processor 302, for example a central processing unit based on 80x86 architecture as designed by Intel™ or AMD™, a system-on-a-chip as designed by ARM™, or any other suitable microprocessor. The processor 302 may be communicatively coupled to auxiliary devices or modules of the 3D environment apparatus 300, using a bus or other coupling. Optionally, the processor 302 and its coupled auxiliary devices or modules may be housed within or coupled to a housing 301, for example, a housing having a form factor of a television, set-top box, smartphone, wearable googles, glasses, or visor, or other form factor.

A user interface device 324 may be coupled to the processor 302 for providing user control input to a process for controlling output of digital cinematic content responsive to sensor data indicating a user's emotional state. The process may include outputting video and audio for a conventional flat screen or projection display device. In some embodiments, the cinematic control process may be, or may include, audio-video output for an immersive mixed reality content display process operated by a mixed reality immersive display engine executing on the processor 302.

User control input may include, for example, selections from a graphical user interface or other input (e.g., textual or directional commands) generated via a touch screen, keyboard, pointing device (e.g., game controller), microphone, motion sensor, camera, or some combination of these or other input devices represented by block 324. Such user interface device 324 may be coupled to the processor 302 via an input/output port 326, for example, a Universal Serial Bus (USB) or equivalent port. Control input may also be provided via a sensor 328 coupled to the processor 302. A sensor may comprise, for example, a motion sensor (e.g., an accelerometer), a position sensor, a camera or camera array (e.g., stereoscopic array), a biometric temperature or pulse sensor, a touch (pressure) sensor, an altimeter, a location sensor (for example, a Global Positioning System (GPS) receiver and controller), a proximity sensor, a motion sensor, a smoke or vapor detector, a gyroscopic position sensor, a radio receiver, a multi-camera tracking sensor/controller, an eye-tracking sensor, a microphone or a microphone array. The sensor or sensors 328 may detect biometric data used as an indicator of the user's emotional state, for example, facial expression, skin temperature, pupil dilation, respiration rate, muscle tension, nervous system activity, or pulse. In addition, the sensor(s) 328 may detect a user's context, for example an identity position, size, orientation and movement of the user's physical environment and of objects in the environment, motion or other state of a user interface display, for example, motion of a virtual-reality headset.

Sensor data from the one or more sensors may be processed locally by the CPU 302 to control display output, and/or transmitted to a server 200 for processing by the server in real time, or for non-real-time processing. As used herein, "real time" refers to processing responsive to user input without any arbitrary delay between inputs and outputs; that is, that reacts as soon as technically feasible. "Non-real time" refers to batch processing or other use of sensor data that is not used to provide immediate control input for controlling the display, but that may control the display after some arbitrary amount of delay.

To enable communication with another node of a computer network, for example the cinematic content server 200, the client 300 may include a network interface 322, e.g., an Ethernet port, wired or wireless. Network communication may be used, for example, to enable multiplayer experiences, including immersive or non-immersive experiences of cinematic content. The system may also be used for non-cinematic multi-user applications, for example social networking, group entertainment experiences, instructional environments, video gaming, and so forth. Network communication can also be used for data transfer between the client and other nodes of the network, for purposes including data processing, content delivery, content control, and tracking. The client may manage communications with other network nodes using a communications module 306 that handles application-level communication needs and lower-level communications protocols, preferably without requiring user management.

A display 320 may be coupled to the processor 302, for example via a graphics processing unit 318 integrated in the processor 302 or in a separate chip. The display 320 may include, for example, a flat screen color liquid crystal (LCD) display illuminated by light-emitting diodes (LEDs) or other lamps, a projector driven by an LCD display or by a digital light processing (DLP) unit, a laser projector, or other digital display device. The display device 320 may be incorporated into a virtual reality headset or other immersive display system. Video output driven by a mixed reality display engine operating on the processor 302, or other application for coordinating user inputs with an immersive content display and/or generating the display, may be provided to the display device 320 and output as a video display to the user. Similarly, an amplifier/speaker or other audio output transducer 316 may be coupled to the processor 302 via an audio processor 312. Audio output correlated to the video output and generated by the media player module 308, cinematic content control engine or other application may be provided to the audio transducer 316 and output as audible sound to the user. The audio processor 312 may receive an analog audio signal from a microphone 314 and convert it to a digital signal for processing by the processor 302. The microphone can be used as a sensor for detection of emotional state and as a device for user input of verbal commands, or for social verbal responses to NPC's or other player actors.

The 3D environment apparatus 300 may further include a random-access memory (RAM) 304 holding program instructions and data for rapid execution or processing by the processor during controlling cinematic content in response to a user's emotional state. When the device 300 is powered off or in an inactive state, program instructions and data may be stored in a long-term memory, for example, a non-volatile magnetic, optical, or electronic memory storage device (not shown). Either or both RAM 304 or the storage device may comprise a non-transitory computer-readable medium holding program instructions, that when executed by the processor 302, cause the device 300 to perform a method or operations as described herein. Program instructions may be written in any suitable high-level language, for example, C, C++, C #, JavaScript, PHP, or Java™, and compiled to produce machine-language code for execution by the processor.

Program instructions may be grouped into functional modules 306, 308, to facilitate coding efficiency and comprehensibility. The modules, even if discernable as divisions or grouping in source code, are not necessarily distinguishable as separate code blocks in machine-level coding. Code bundles directed toward a specific type of function may be considered to comprise a module, regardless of whether or not machine code on the bundle can be executed independently of other machine code. The modules may be high-level modules only. The media player module 308 may perform operations of any method described herein, and equivalent methods, in whole or in part. Operations may be performed independently or in cooperation with another network node or nodes, for example, the server 200.

Figure 4:
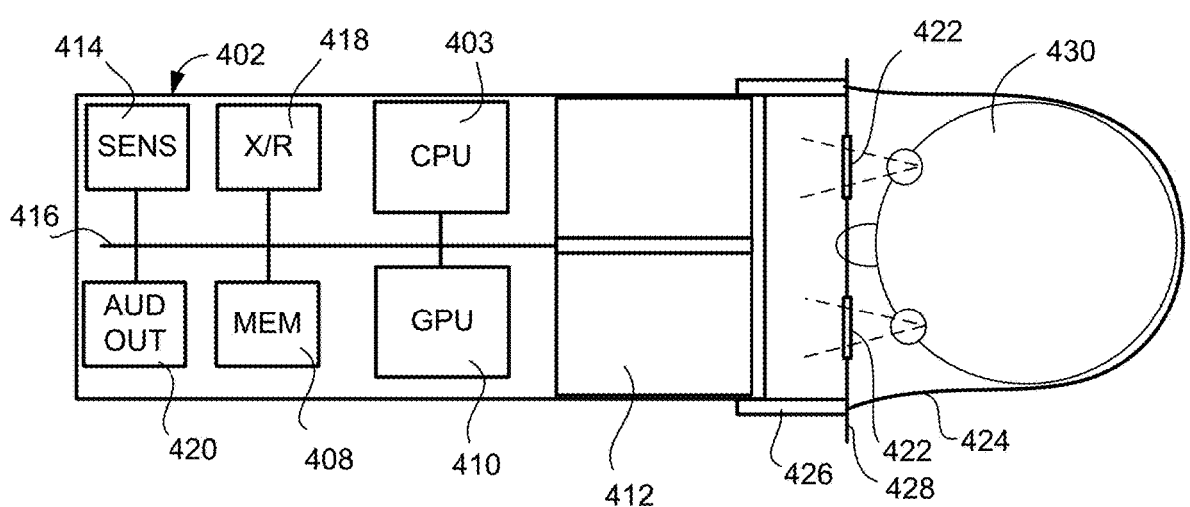
FIG. 4 is a schematic diagram showing features of a virtual-reality client device for controlling output of digital cinematic content responsive to sensor data indicating a user's emotional state.

In addition to conventional 2D output or 3D output for display on two-dimensional (flat or curved) screens (e.g., by televisions, mobile screens, or projectors), the cinematic control methods disclosed herein may be used with Virtual Reality (VR) or Augmented Reality (AR) output devices. FIG. 4 is a schematic diagram illustrating one type of immersive VR stereoscopic display device 400, as an example of the client 300 in a more specific form factor. The client device 300 may be provided in various form factors, of which device 400 provides but one example. The innovative methods, apparatus and systems described herein are not limited to a single form factor but may be used in any video output device suitable for cinematic output. As used herein, cinematic output includes any digital signal that produces audio-video output according to a script or narrative, which may be branching and interactive. In an aspect, the cinematic content varies in response to a detected emotional state of the user.

The immersive VR stereoscopic display device 400 may include a tablet support structure made of an opaque lightweight structural material (e.g., a rigid polymer, aluminum or cardboard) configured for supporting and allowing for removable placement of a portable tablet computing or smartphone device including a high-resolution display screen, for example, an LCD display. The device 400 is designed to be worn close to the user's face, enabling a wide field of view using a small screen size such as in smartphone. The support structure 426 holds a pair of lenses 422 in relation to the display screen 412. The lenses may be configured to enable the user to comfortably focus on the display screen 412 which may be held approximately one to three inches from the user's eyes.

The device 400 may further include a viewing shroud (not shown) coupled to the support structure 426 and configured of a soft, flexible or other suitable opaque material for form fitting to the user's face and blocking outside light. The shroud may be configured to ensure that the only visible light source to the user is the display screen 412, enhancing the immersive effect of using the device 400. A screen divider may be used to separate the screen 412 into independently driven stereoscopic regions, each of which is visible only through a corresponding one of the lenses 422. Hence, the immersive VR stereoscopic display device 400 may be used to provide stereoscopic display output, providing a more realistic perception of 3D space for the user.

The immersive VR stereoscopic display device 400 may further comprise a bridge (not shown) for positioning over the user's nose, to facilitate accurate positioning of the lenses 422 with respect to the user's eyes. The device 400 may further comprise an elastic strap or band 424, or other headwear for fitting around the user's head and holding the device 400 to the user's head.

The immersive VR stereoscopic display device 400 may include additional electronic components of a display and communications unit 402 (e.g., a tablet computer or smartphone) in relation to a user's head 430. When wearing the support 426, the user views the display 412 though the pair of lenses 422. The display 412 may be driven by the Central Processing Unit (CPU) 403 and/or Graphics Processing Unit (GPU) 410 via an internal bus 417. Components of the display and communications unit 402 may further include, for example, a transmit/receive component or components 418, enabling wireless communication between the CPU and an external server via a wireless coupling. The transmit/receive component 418 may operate using any suitable high-bandwidth wireless technology or protocol, including, for example, cellular telephone technologies such as 3rd Generation Partnership Project (3GPP) Long Term Evolution (LTE), Global System for Mobile communications (GSM) or Universal Mobile Telecommunications System (UMTS), and/or a wireless local area network (WLAN) technology for example using a protocol such as Institute of Electrical and Electronics Engineers (IEEE) 802.11. The transmit/receive component or components 418 may enable streaming of video data to the display and communications unit 402 from a local or remote video server, and uplink transmission of sensor and other data to the local or remote video server for control or audience response techniques as described herein.

Components of the display and communications unit 402 may further include, for example, one or more sensors 414 coupled to the CPU 403 via the communications bus 417. Such sensors may include, for example, an accelerometer/inclinometer array providing orientation data for indicating an orientation of the display and communications unit 402. As the display and communications unit 402 is fixed to the user's head 430, this data may also be calibrated to indicate an orientation of the head 430. The one or more sensors 414 may further include, for example, a Global Positioning System (GPS) sensor indicating a geographic position of the user. The one or more sensors 414 may further include, for example, a camera or image sensor positioned to detect an orientation of one or more of the user's eyes, or to capture video images of the user's physical environment (for VR mixed reality), or both. In some embodiments, a camera, image sensor, or other sensor configured to detect a user's eyes or eye movements may be mounted in the support structure 426 and coupled to the CPU 403 via the bus 416 and a serial bus port (not shown), for example, a Universal Serial Bus (USB) or other suitable communications port. The one or more sensors 414 may further include, for example, an interferometer positioned in the support structure 404 and configured to indicate a surface contour to the user's eyes. The one or more sensors 414 may further include, for example, a microphone, array or microphones, or other audio input transducer for detecting spoken user commands or verbal and non-verbal audible reactions to display output. The one or more sensors may include, for example, electrodes or microphone to sense heart rate, a temperature sensor configured for sensing skin or body temperature of the user, an image sensor coupled to an analysis module to detect facial expression or pupil dilation, a microphone to detect verbal and nonverbal utterances, or other biometric sensors for collecting biofeedback data including nervous system responses capable of indicating emotion via algorithmic processing.

Components of the display and communications unit 402 may further include, for example, an audio output transducer 420, for example a speaker or piezoelectric transducer in the display and communications unit 402 or audio output port for headphones or other audio output transducer mounted in headgear 424 or the like. The audio output device may provide surround sound, multichannel audio, so-called 'object-oriented audio', or other audio track output accompanying a stereoscopic immersive VR video display content. Components of the display and communications unit 402 may further include, for example, a memory device 408 coupled to the CPU 403 via a memory bus. The memory 408 may store, for example, program instructions that when executed by the processor cause the apparatus 400 to perform operations as described herein. The memory 408 may also store data, for example, audio-video data in a library or buffered during streaming from a network node.

Figure 5:
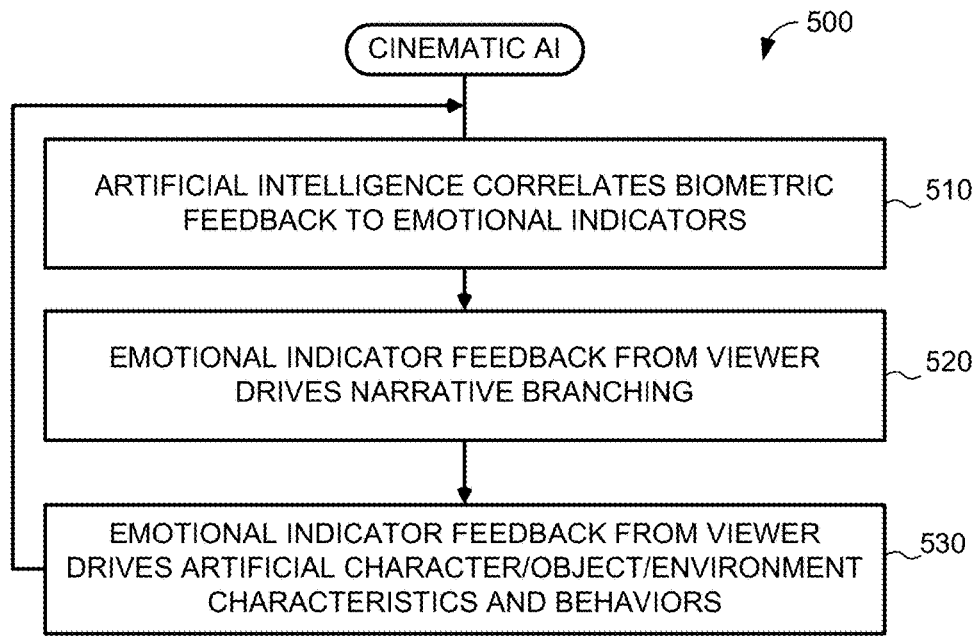
FIG. 5 is a flow chart illustrating high-level operation of a method for producing or controlling output of digital cinematic content responsive to sensor data indicating a user's emotional state.

Having described examples of suitable clients, servers, and networks for performing methods of controlling output of digital cinematic content responsive to sensor data indicating a user's emotional state, more detailed aspects of these methods will be addressed. FIG. 5 illustrates an overview of the methods 500, which may include three related operations in any functional order or in parallel. A correlating operation 510 uses a machine learning algorithm to correlate biometric data for a user or user cohort to an emotional indicator. Optionally, the machine learning algorithm may be configured to process context-indicating data in addition to biometric data, which may improve accuracy. Context-indicating data may include, for example, user location, user position, time-of-day, day-of-week, ambient light level, ambient noise level, and so forth. For example, if the user's context is full of distractions, biofeedback data may have a different significance than in a quiet environment. An emotional indicator may be a symbolic value that relates to an emotional arc. The indicator may have constituent elements, which may be quantitative or non-quantitative. For example, an indicator may be designed as a multi-dimensional vector with values representing intensity of psychological qualities such as cognitive load, arousal, and valence. Valence in psychology is the state of attractiveness or desirability of an event, object or situation; valence is said to be positive when a subject feels something is good or attractive and negative when the subject feels the object is repellant or bad. Arousal is the state of alertness and attentiveness of the subject. The machine learning algorithms may include at least one supervised machine learning (SML) algorithm, for example, one or more of a linear regression algorithm, a neural network algorithm, a support vector algorithm, a naïve Bayes algorithm, a linear classification module or a random forest algorithm.

A narrative branching operation 520 selects destination branches at narrative forks of cinematic content, based on emotional indicators, predictions of emotional response, and a targeted emotional arc for the user or cohort. A participating control node may make predictions using machine learning tools to predict narrative elements likely to produce a targeted emotional state in the user or cohort. Once making the prediction, the control node selects the branch having the combination of elements scored as most likely to produce the targeted emotional response. In addition, the control node may base the branching decision partly on player actor direct input in a manner resembling an interactive video game, by weighing direct input together with emotional indicators. Direct user input may include, for example, spoken or texted verbal input, input from a game controller, bodily movement detected by a camera array, or selection of control links in a user interface. Further, the control node may base the branching decision partly on contextual indicators, such as dialog with NPC's or other player actors.

A cinematic content control node may be configured to change the characteristics or behaviors of characters, objects, or environments appearing in cinematic content (collectively, "supportive content"), with or without altering the narrative. A supportive content selection operation 530 selects characteristics and behaviors of audio-video elements based on based on emotional indicators, predictions of emotional response, and a targeted emotional arc for the user or cohort. Supportive content selection may predict responses to changes and weigh emotional inputs with user inputs, using techniques that parallel branch selection. For example, a first user's past responses may indicate an association between the color red and happiness, while a second user's responses indicate an association between green and happiness. For scenes intended to be happy, the supportive content selection operation may cause more red objects to be displayed for the first user, and more green objects for the second user. More complex supportive content selection may include character interactions, which is discussed further herein below.

How do you quantize emotion? Emotions cannot be measured directly therefore we must measure sentic modulation. Sentic modulations are modulations of biometric waveforms attributed to emotional states or changes in emotional states. In an aspect, to obtain baseline correlations between sentic modulations and emotional states, player actors may be shown a known visual stimulus (e.g., from focus group testing or a personal calibration session) to elicit a certain type of emotion. While under the stimulus, the test module may capture the player actor's biometric data and compare stimulus biometric data to resting biometric data to identify sentic modulation in biometric data waveforms.

Figure 6:
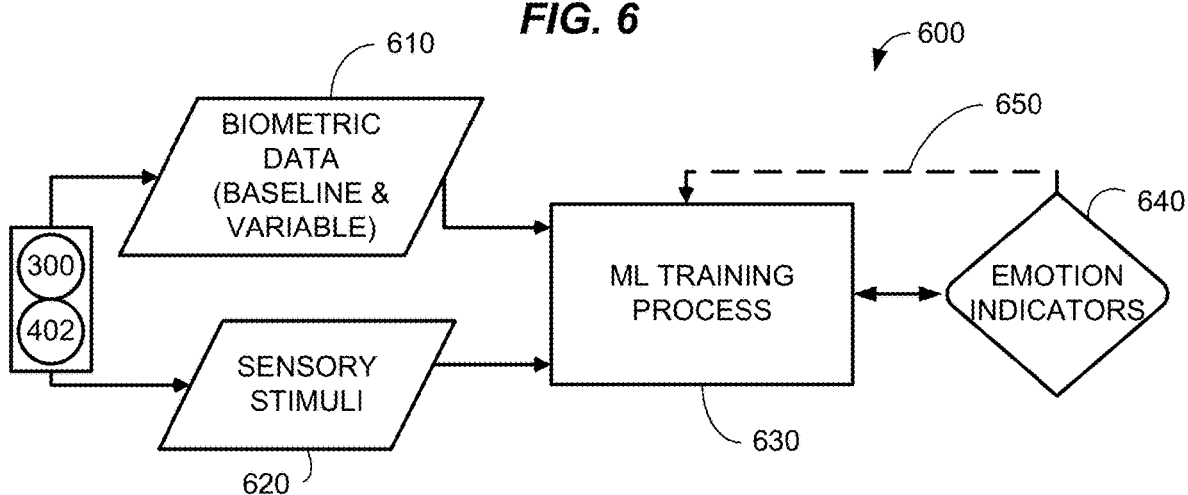
FIG. 6 is a block diagram illustrating high-level aspects of a system for controlling output of digital cinematic content responsive to sensor data indicating a user's emotional state.

Machine learning, also called AI, can be an efficient tool for uncovering correlations between complex phenomena. As shown in FIG. 6, a system 600 for controlling output of digital cinematic content responsive to sensor data 610 indicating a user's emotional state may use a machine learning training process 630 to detect correlations between audio-video and narrative stimuli 620 and biometric data 610. The training process 630 may receive stimuli data 620 that is time-correlated to the biometric data 610 from media player clients (e.g., clients 300, 402). The data may be associated with a specific user or cohort or may be generic. Both types of input data (associated with a user and generic) may be used together. Generic input data can be used to calibrate a baseline for emotional response, to classify a baseline emotional response to a scene or arrangement of cinematographic elements. If most users exhibit similar biometric tells when viewing a scene within a narrative context, the scene can be classified with other scenes that provoke similar biometric data from users. The similar scenes may be collected and reviewed by a human creative producer, who may score the scenes on emotional indicator metrics 640 manually, assisted by automated analysis tools. In an alternative, the indicator data 640 can be scored by human and semi-automatic processing without being classed with similar scenes. These human-scored elements become training data for the machine learning process 630. In some embodiments, humans scoring elements of the cinematic content may include the users, such as via online survey forms. Scoring should consider cultural demographics and may be informed by expert information about responses of different cultures to scene elements.

The ML training process 630 compares human and machine-determined scores of scenes or other cinematographic elements and uses iterative machine learning methods as known in the art to reduce error between the training data and its own estimates. Creative content analysts may score data from multiple users based on their professional judgment and experience. Individual users may score their own content. For example, users willing to assist in training their personal "director software" to recognize their emotional states might score their own emotions while watching content. A problem with this approach is that the user scoring may interfere with their normal reactions, misleading the machine learning algorithm. Other training approaches include clinical testing of subject biometric responses over short content segments, followed by surveying the clinical subjects regarding their emotional states. A combination of these and other approaches may be used to develop training data for the machine learning process 630.

Once the process has learned correlations for a user or group of users, it is ready to apply its learned correlations during real-time content consumption. Multilevel AI loops inform cooperating software modules for Cinematic AI. Trials explore past AI successes and identify opportunities to achieve goals using AI tools. Procedures implement the AI tools used in each trial. Rewards incentivize application of the tools when goals are achieved.

Story management software may be used to implement a method for creating multilevel AI loops for each player actor. Loops may include, for example, a story world loop, a non-player character (NPC) loop, and a player actor loop. In a story world AI loop, stories are enabled according to an emotional plan or "arc" as a goal and adapted in real time to achieve the goal by detecting emotions of a player actor interacting with NPCs, optionally viewing immersive content using a VR or AR headset. In an NPC AI loop, the goal is to elicit a specific story element emotion by controlling NPC interactions with the player actor. In a player actor AI loop, the AI is directed to correctly identifying sentic modulations in biometric data and corresponding emotions of the player actor.

Figure 7:
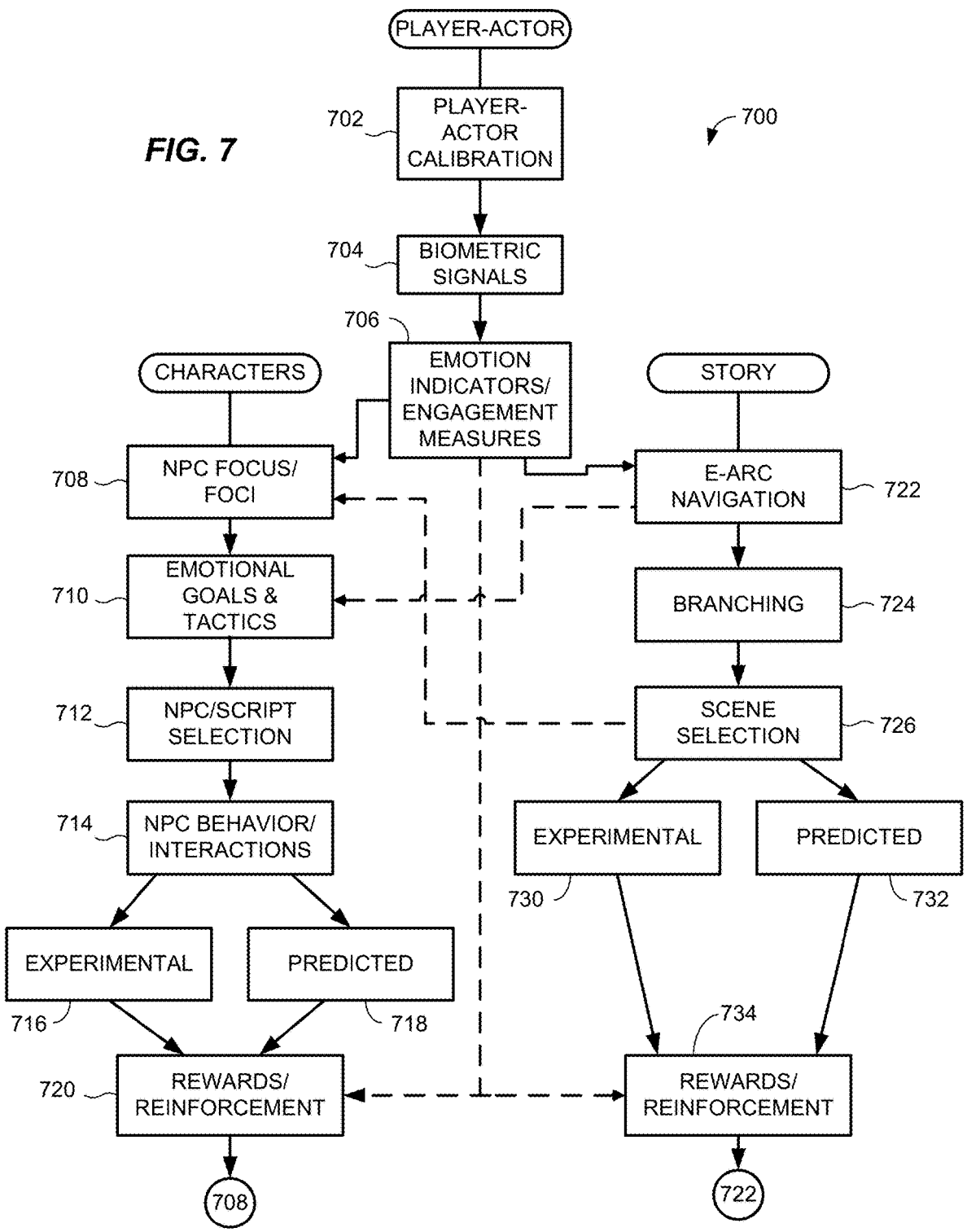
FIG. 7 is a flow diagram showing aspects of a method for controlling output of digital cinematic content responsive to sensor data indicating a user's emotional state.

FIG. 7 shows aspects of a method 700 for controlling output of digital cinematic content responsive to sensor data indicating a user's emotional state, using cooperating AI loops. The method 700 provides a more detailed example of the methods overview 500 illustrated by FIG. 5, in which a player actor interacts with a story arc and with computer-controlled characters (e.g., "bots" or NPCs) that play roles within the cinematic content. Such characters are an example of supportive content, which supports but does not nullify the narrative and emotional arcs that the cinematic content is designed to follow.

Blocks 702-704 correspond to a player actor loop. At 702, a media player calibrates itself for use by a player actor. This may include training of a machine learning algorithm, taking baseline measurements, downloading available calibration data from a server for use in a session with the player actor, or other customization. In an aspect, calibration is designed to be as unobtrusive as possible. For example, calibration by the media player, alone or in cooperation with one or more artificial intelligence (AI) servers, may occur continuously or at intervals and gradually improve with time as the system builds a more accurate emotional profile of the user. In addition to resting physiology sensor calibration, the calibration system may also normalize biometric data between player actors to establish a baseline for comparing biometric responses between players. An additional content expectation normalization may also be measured to quantify player expectation of content. This process may include the measurement of biometric responses while under representative stimulus content. Calibration and normalization, when used together, provide a robust baseline methodology for computing both singular and aggregate biometric responses between players. The calibration and normalization factors may be used to compute emotional responses and engagement with content.

At 704, the media player begins playing the cinematic content and the player actor begins viewing it while the media player's sensors begin detecting biometric signals used for emotional indication. Biometric sensors used to detect the biometric signals are known in medical fields and may be adapted for sensing in the present application. For example, sensors developed for medical uses capable of monitoring physiological signals may include, for example, electromyography (EMG) sensors that sense electrical activity produced by skeletal muscles, electroencephalography (EEG) sensors that detect electrical activity in the brain, galvanic Skin Response (GSR) sensors that detect changes in the electrical resistance of the skin, electrocardiogram (ECG/EKG) sensors that detect heartbeat; optical sensors that detect body language, facial expressions, gaze direction and corneal deformation, brain-computer interface (BCI) signals that directly connect an enhanced brain with a coupled machined (e.g., the media player or an intermediate machine) with or without bidirectional communication capability between the brain and the coupled machine, and microphones for audio analysis to detecting emotional indicators such as voice modulation.

At 706, the system (e.g., the media player, optionally with participation by network nodes) digitizes and processes sensor data, thereby deriving symbolic emotional indicators that can be correlated by story-telling software to emotional targets of a story arc. Machine learning/AI tools may be used to process the sensor data and derive indicators in real time. The emotional indicators may be, or may include, quantitative measures of symbolized emotional qualities, preferably in a compact form. For example, a 64-bit machine-readable value is capable of conveying a value of 21 different emotional qualities in a scale from zero to eight, in which the identity of the quality is conveyed by bit position of its value. For example, the first three bits may indicate a happiness value, the second three bits a tension value, and so forth. Schemes for indicating emotions in machine-readable data are described in more detail herein below.

Blocks 708-720 correspond to a non-player character (NPC) loop. At 708, a processor of the media player determines a focus or foci on one or more NPCs. Relevant input to the determination 708 may include emotional indicators from the player actor loop (block 706) and a scene identifier from the story loop (block 726). From the scene data, the processor narrows the list of available NPCs to those available for the scene at hand, for example using a database query to retrieve all NPC identifiers that the content designers have associated with the scene. The player actor's current emotional state from process 706 is used at a later stage described below.

Further relevant input to process 708 may include the NPCs' emotional impact scores. Each NPC may be associated with a predetermined emotional impact score, which may be generic or customized for the player actor. For example, a young child NPC might be scored high on a generic sympathy scale and low on a sympathy scale customized for a player actor who has an aversion to children. The emotional impact score is a predictive value based on experience of the content designer and/or empirical data. When well-crafted, the NPC's emotional impact score will predict the emotional reactions the NPC is most likely to evoke in the player actor. For example, a cute child NPC might score high on sympathy and low on fear. Similarly, the process 708 may select a tactic for the NPC to use, e.g., confrontation, reassurance, and so forth. Each NPC may be associated with one or more tactics suitable for its emotional profile.

Before selecting an NPC based on emotional impact score, the processor determines an emotional goal or goals for the player actor at 710. For example, the processor may determine from the emotional arc navigation process at 722 that a targeted emotion for the player actor is suspenseful anxiety for the scene identified at 726. Having received a current player actor emotional indicator value from the process 706 via its upstream process 708, the goal-setting process 710 may compare the current value with the targeted value and determine an error. For example, suppose the target is suspense but the current emotional state indicator indicates that the player actor is bored. In response, the goal-setting process sets a goal of moving the player actor from boredom to suspense. The process 710 may provide the goal to downstream process 712, which selects an NPC and script for the NPC to operate. In an alternative, the process may select a different tactic for the NPC to follow, which may be associated with different scripts. Continuing the example, the selection process may select an NPC with an emotional impact profile that scores highly for transforming disinterest into suspense for the player actor, and a script that scores highly in the same category.

At 714, the processor operates the selected NPC according to the selected script. The script may be interactive, such that the NPC behaves differently based on player actor direct interaction with it or on updated emotional indicators. In an aspect, the process 714 may operate a predicted script illustrated at 718. The predicted script is the one predicted by the process 714 to be most likely able to correct the player actor's deviation from the targeted arc. If the predicted script fails, or based on random or quasi-random factors, the process 714 may operate an experimental script illustrated at 716. Experimental scripts test the player actor's response to untried circumstance. Such scripts may be useful to avoid payer actor boredom with repeated scripts or themes, or when predicted response data is lacking.

At 720, the processor records the emotional effect of the NPC and script in the relevant data structures used for training the AI algorithms responsible for NPC and script selection. Successes and failures thereby become new data for use in improving the future effectiveness of the method 700 in using NPC interaction to nudge player actors towards an emotional target. If the nudging is unsuccessful, the process may select and implement a different NPC, tactic, or script at any point when the emotional sensor data indicates that the targeted reaction is not being elicited from the player actor. The method 708 may revert to block 708 for the next scene.

Blocks 722-734 correspond to a story loop. The story loop proceeds similarly to the NPC loop, but is directed to scene selection for the main cinematic content instead of NPC selection and behavior. At 722, the processor compares the player actor's current emotional indicator to an emotional arc defined in digital data for the story. Examples of emotional arcs are described herein below. At 724, the processor selects a narrative branch based on predictive AI for the player actor. The AI predicts which narrative branch is most likely to result in the player actor experiencing the director's emotional arc, based on an emotional impact score for the branch, which may be an aggregate of emotional impact scores for the scenes that the branch contains. At 726, the processor selects the next scene in the narrative branch, again based on emotional impact and an estimation of error. A single narrative branch may contain alternative scenes that do not change the main story line but are tailored for greater emotional impact for users. For example, the same story may be told using different scenes for child and adult player actors. If the processor detects no emotional error, it may use a default scene or branch.

At 730 and 732, the processor selects a scene based on a predictive analysis 732, or an experimental trial 730. Predicted and experimental scenes may be selected by the processor based on the same or similar factors used to decide between predicted and experimental NPCs and scripts. At 734, the processor records the measured emotional response for improving future AI predictions. Thus, a player actor loop, NPC loop, and story loop may run concurrently and cooperatively to actively implement schemes that interact with sentic modulations of player actors, including the branch, scene and NPC control schemes for influencing player actors towards targeted emotional arcs as outlined above.

Multiple stories can be programmed into cinematic content produced for cinematic AI. Story elements can be combined in countless ways by AI engines reacting to emotional feedback from player actors, producing story patterns that content designers only dimly apprehend if at all during the creative process. Too much variety can become a technical weakness, if many varieties are unappealing. The technical challenge is to improve the frequency with which users find their own version of cinematic content appealing to watch and spend social time discussing. Hit the mark with high frequency, and the amount of variety will be an asset, not a liability. Player actors will have a new pastime: comparing personal versions. When personally identifiable viewing history is kept under the control of the subject, its social value as "knowledge for friends only" creates economic value for the creators of the information even if the creators have no access to the information. As material for private social exchange, its value is in creating demand for the cinematic content.

Data on emotional reactions and AI choices will have economic value stripped of personal identifying information, as well. Thus sterilized, researchers and creators can study the data using AI tools Cinematic AI to understand usage trend and design new content. Emotional proxy ('tells') information that tracks (links with) certain attributes or other relevant story/arc/experience components from single users or cohorts may be used to guide generation of more stories or arcs or experience attributes, besides driving of-the-moment, real-time content flow. Emotion indicators gathered from single users or cohorts of users to feed the story management process has additional value for contouring new content (e.g. the next chapter of a story, level of a game, episode of episodic fare, sequel to a movie, and so forth), producing trailers for marketing and promotion, or green-lighting prospective story ideas, based on that information. In addition, the de-personalized data may be useful for user ratings of content, as described in connection with the accompanying Appendix and FIG. 9B below.

As noted in connection with FIG. 7, in one approach story branches are triggered by player actor emotions which provide a feedback loop into the story management software. Story management software controls the environment and artificial character inclusion and goals. Writers and directors train the story management AI but the AI controls the emergent stories possible by player actor interactions & emotions One technique for improving success frequency may be to use story element emotional codes, also called scores. Story management software changes scenes and NPCs based on NPC goals to designed to elicit emotions from player actors. Emotional responses will be mapped to common story elements including, for example, point of attack, inciting incident, climax, first culmination, and resolution. Story element emotional codes allow for dynamic emotional branching in various patterns.

Figure 8:
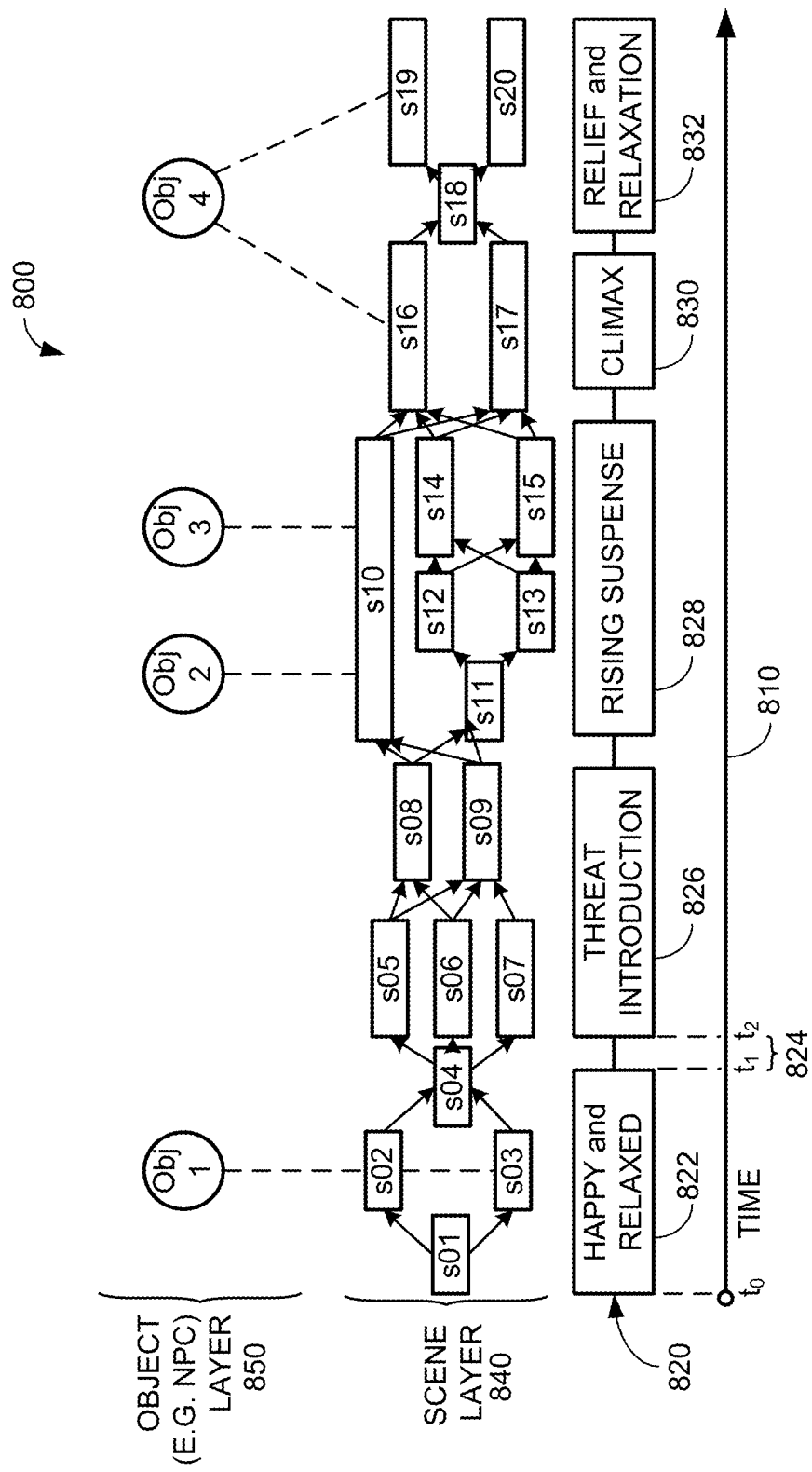
FIG. 8 is a concept diagram illustrating a map of layers and branching of digital cinematic content with an emotional arc responsive to sensor data indicating a user's emotional state.

FIG. 8 shows a map 800 of layers and branching of digital cinematic content with an emotional arc 820 responsive to sensor data indicating a user's emotional state. The map is time-correlated against a timeline 810 beginning at initial time $t_0$. The emotional arc 820 includes a sequence of target periods that summarize predominate emotions during a time interval. For example, a predominate emotion in the first segment 822 is happy and relaxed, in the second interval 826 threat awareness (mild fear), in a third interval 828 rising suspense, in the fourth interval 830 climax (excitement), in the fifth interval 832 relief and relaxation. The intervals may be separated by transition periods, a first 824 between times $t_1$ and $t_2$, in which emotions overlap. Emotion arcs may be modeled by other models. For example, instead of a chain of intervals 820, an emotional arc may be modeled as a vector of periodically (e.g., every 5 seconds or less) updated variable values, wherein each value of the vector represents a quantitative value of an emotional quality. The division into segments of predominate emotion is merely a convenient summary.

Scene layer 840 may be, or may include, a directed acyclic graph (DAG) of nodes (e.g., nodes s01-s20). A story tree is a restricted form of DAG, in which each child node can have only one parent. Scene layers can be arranged in trees, or in any other DAG. FIG. 8 shows a scene layer 840 in a DAG not restricted to a tree. Some downstream scenes can have more than one parent, and the layer can separate into parallel chains in spots. For example, scene s04 has two parents, s02 and s03. Scenes s12-s14 form competing parallel subchains. Each scene has a definite length in time. For example, story software may define a maximum length of time for interactive scenes as the maximum time allowed for NPC's or scenes to reach an emotional target before giving up. Gaps are shown between scenes merely for illustrative separation. In most cinematic content, each scene should fit or blend smoothly with the next. Gaps may be avoided by predicting each player actor's preferences to delete certain scenes or moments, for example, based on prior offline data or an initial calibration exercise. In this manner, knowing that some gaps would otherwise occur if certain scenes or moments were to be abridged, the story controller may call up replacement scene or moments, or implement seamless 'branching' to an appropriate next node or set of nodes to avoid gaps.

Object layer 850 holds any emotion-influencing objects that appear in any scene, affect the appearance or any scene, or change the audio content of any scene. Objects can include interactive NPCs and their scripts as previously described, props, backgrounds, environments, lighting schemes, surface colors and textures, audio tracks, or any other object in a scene that is controlled to evoke an emotional response in a player actor. In layer 850, a first object 'Obj. 1' can appear or operate in scenes s01-s02. Second and third objects 'Obj. 2' and 'Obj. 3' appear or operate in long scene s10 only. A fourth object 'Obj. 4' can appear or operate in both scenes s16 or s19. Few objects are shown in the map 800 for illustrative simplicity. In an actual map of most cinematic content, most scenes will be associated with numerous different objects. Although the map 800 is simplified, it illustrates an example of a map such as may be used to provide structure and guidance to cinematic AI during a multi-loop control process 700 as illustrated in FIG. 7.

Figure 9A:
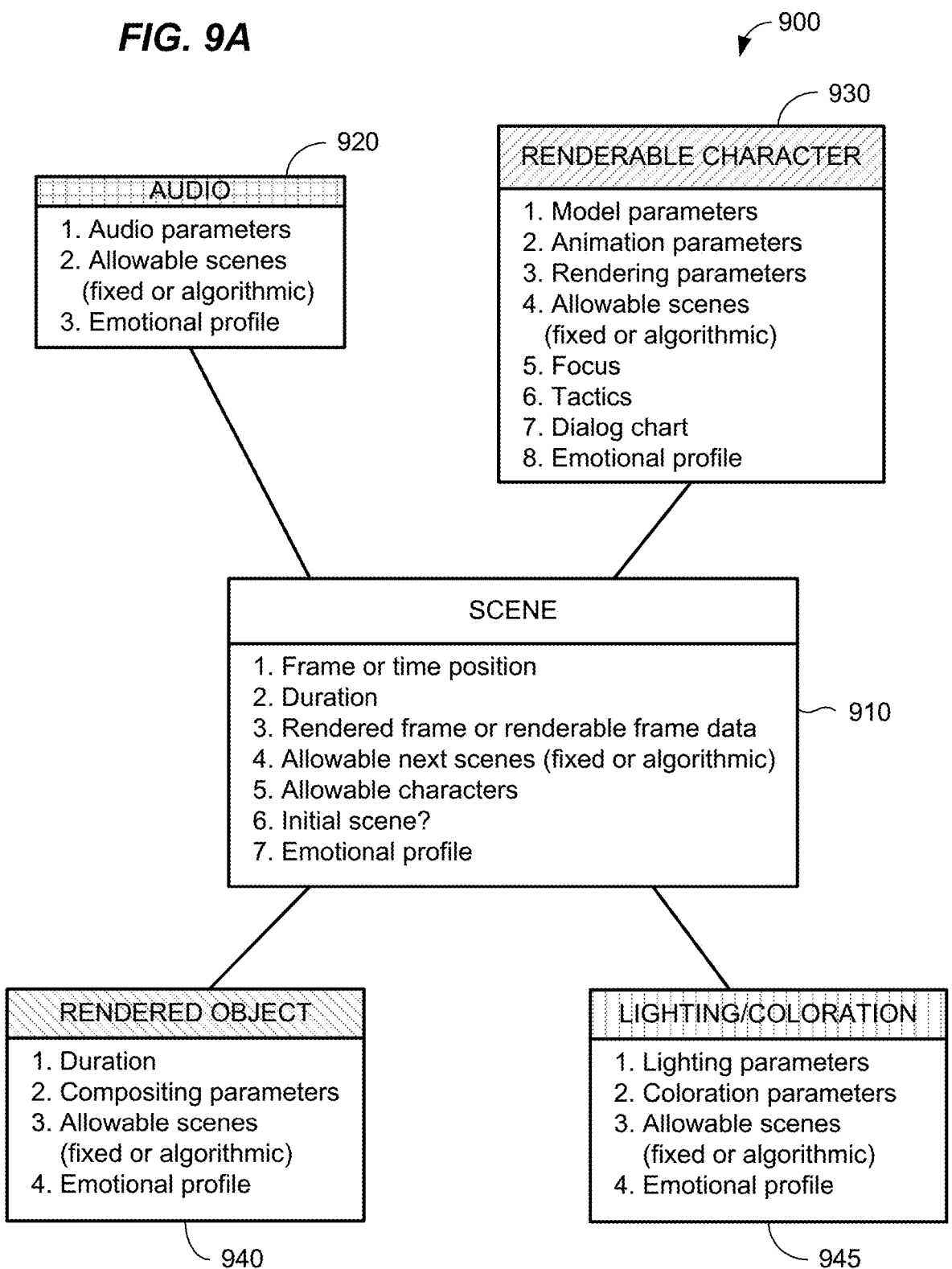
FIG. 9A is a block diagram illustrating metadata and associations between different objects and a scene in cinematic content as mapped in FIG. 8.

FIG. 9A shows a metadata and association system 900 between different objects and a scene in cinematic content as mapped in FIG. 8. The scene 910 is itself an object and may be characterized by scene metadata, for example, a frame or time position in a timeline, a duration (e.g., in seconds or number of frames), a link to rendered data and/or frame data that is renderable at run time, identifiers for allowable next scenes, an indication whether the scene is an initial scene (i.e., has no parent scene), and an emotional impact score, also called an emotional profile. Supporting scene objects may include, for example, an audio object or objects 920, renderable character (e.g., interactive NPC) or characters 930, rendered object or objects 940, and lighting/coloration object or objects 945. Objects may further include NPC scripts, which are not shown.

Each audio object 920 may be characterized by metadata including, for example, audio parameter including a link to the digital audio data and play parameters, allowable scenes, which may be fixed list or algorithmically determined at run time, and an emotional profile. Allowable scene and emotional profile (impact score) are present in metadata for every object shown in system 900. In addition, each renderable character object 930 metadata may be characterized by model parameters, e.g., its geometry and surface properties, its animation parameters, its rendering parameters, and a dialog chart or link to a sub-object of NPC scripts. Each rendered object 940 metadata may be characterized by a duration and compositing parameters for blending the rendered object with a scene. Each lighting/coloration object 945 may be characterized by metadata including lighting parameters and coloration parameters. The illustrated parameters and metadata are merely examples.

Figure 9B:
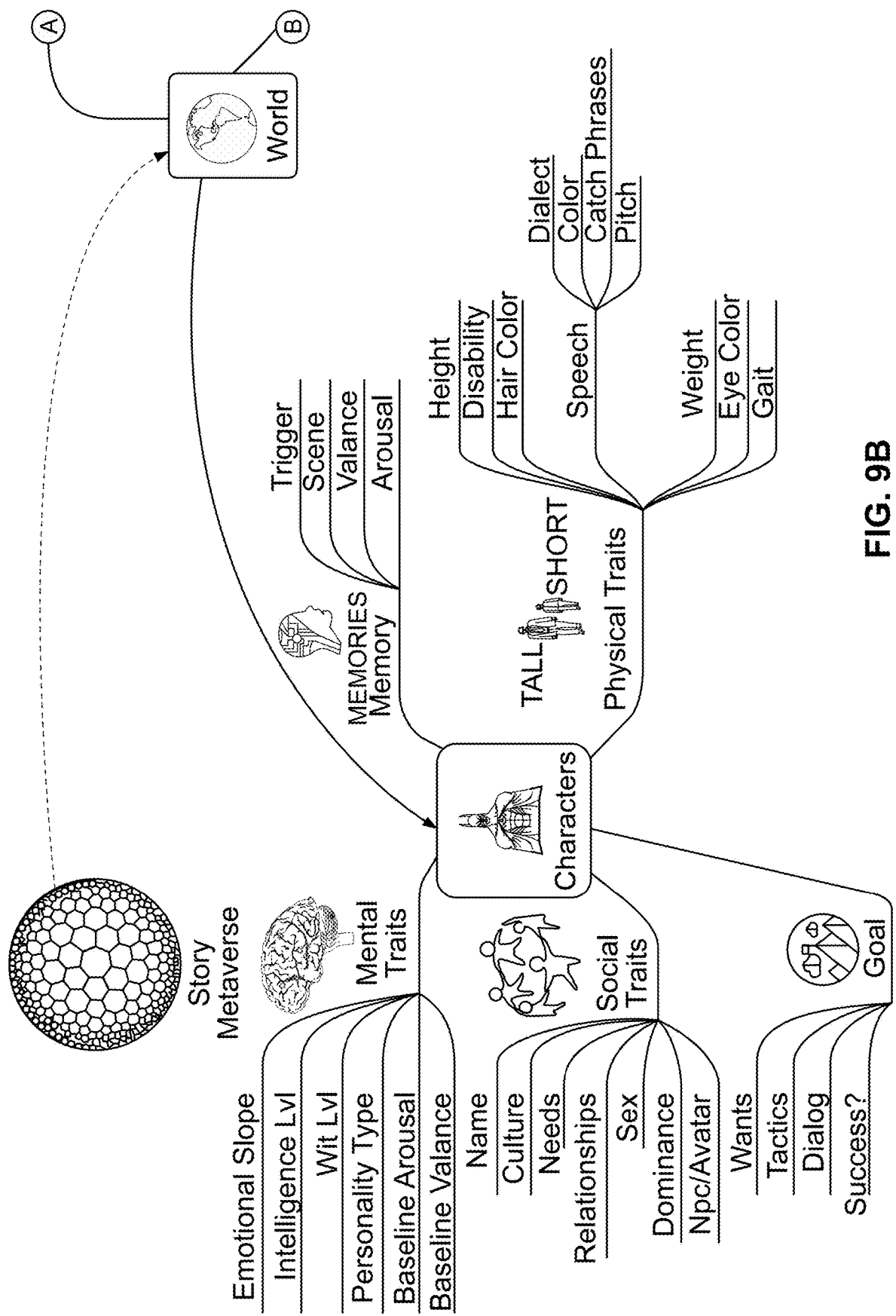
FIG. 9B is a hierarchical network diagram showing relationships between characters, stories and emotional arcs.

FIG. 9B shows more detailed aspects or characters and stories arranged in a tree hierarchy 950. A data structure may show relationships between the objects or other story nodes and every possible permutation of the story. For example, a data structure may be, or may include, a LUT (Look Up Table) per story, theme, emotional arc, sequence, scene and characters in the scene. This binary LUT may include every possible permutation and choice for a corresponding story world. Because characters may be encoded as having goals and tactics, the characters either achieve their goals or not. For example, a scene may be mapped into as a tree of binary choices and outcomes for each character and situation a player actor can possibly experience. These relationships together with the relevant player actor interactions and emotional codes may form the basis for every decision to be made in a story. The story software may use subconscious input data and emotions to discern user choices as inputs to address the LUT.

In an alternative, story software may not necessarily encode every possible combination, for at least two reasons: first, some variations are so like others that different paths don't make much of an impact and, so, don't matter much; and second, an 'embedded playback chain' (as in DVD for example) may pre-encode in each relevant node block how to proceed on the next selected path. For example, in a version 1 case, jump to node X next; in a version 2 case, the same current node dictates a jump to node Y next. In each case the next node also has pre-encoded instructions to direct the path to the associated next node (e.g. version 1, 2, and so forth). If the viewer changes her mind or her emotional indicators suggest a change in some path, the playback chain will handle the change without upset. Each node contains code or metadata encoding the next story node depending on the node path taken by the player actor to reach the current node. In summary, either the story software may encode an overarching LUT with all possible permutations, or an embedded playback chain may simplify the possibilities to those that are expected to make a difference in the player actor's experience.

Characters may possess simulated traits which may be conceptually arranged in classes, such as mental traits, social traits, physical traits and memories (e.g., back stories). Each trait may be modeled using an algorithm characterized by parameters. A neural network provides an example of a non-deterministic algorithm for modeling traits. The network may be trained using reactions of a model character to various stimuli, and once trained may govern the character's output for old and new stimuli alike. A story engine may also use a deterministic algorithm, for example, stimuli may be represented by an input vector that the story software multiplies by a matrix to produce an output vector. Different matrices may be used to model different traits, or a unified matrix may include values for various traits that work together to transform an input stimulus into an output action.

A character's mental traits may include, for example, emotional slope that determines how quickly the character's emotions react to input, intelligence level, with level, personality type (e.g., Meyers-Briggs or other scale), and baseline levels of valence and arousal. A character's social traits may include, for example, name, culture, social needs, relationships, sexual preferences, level of dominance, and social preferences in NPC's and avatars. A character's goals may include, for example, wants or desires, preferred and available tactics, specific dialog, and measures of success.

Non-player character objects may be programmed as having goals and tactics, including dialog. Characters either achieve their goals or not, so any dialog scene may be analyzed as a collection of binary outcomes for each character and situation the player actor could ever be in. Dialog may include speech and body language or other actions (a glance, a gesture, a wordless utterance, etc.). A "dialog scene" may not even include words. Choices can and often are apparent even when no words (or few words) are spoken and story software can take this into account. For that matter, when irony, deception or other natural language operators are in play, explicit literal words may be misleading since the words may belie the actual choices that are being made by characters in a drama.

Memory traits may include triggers, narrative drivers for scenes, and past experiences with valence and arousal in response to stimuli. Physical traits that are modeled by the software engine may include, for example, height, disability, abilities, speech patterns, and appearance.

Characters fit into the story world (which may itself be part of a larger story universe). The story world accommodates the characters, relationships between characters and between characters and avatars, and stories. Stories may be characterized by high-level code and may include lower-level elements such as theme, sequences, acts (groups of scenes), scenes, and emotional targets (e.g., arousal, valence). Themes may be characterized by emotional arcs, musical scores, and environmental design (e.g., sets, lighting, and camera parameters).

In an aspect, story software is encoded to determine which emotional arcs are the most effective by measuring and computing sentic modulation power. The story controller may measure both prior to the experience (to measure expectation power) versus stimulus power (average power while under stimulus) throughout the experience. A basic computational equation may be, or may include: Player Actor Enjoyment=Average (stimulus sentic modulation power)−(expectation sentic modulation power), wherein average stimulation power is averaged across time while under stimulus content, and expectation power is measured prior to stimulus content (baseline mood measurement & question response measurement). Because emotions come in waves and are detected by a superposition of different signals, story software may be encoded to compute root mean square (RMS) values of input signals to represent the time varying signals. In addition, the control algorithm may assign weights to different signals. The result of the equation may include an empirical value for how much a consumer was affected by the content. The greater the number, the more the consumer liked the content versus the more negative the number.

In an aspect, this data from multiple users may be aggregated together to get an empirical value for the strength (power) of any piece of content. The aggregate data may provide an empirical box office rating as an alternative to textual reviews or arbitrary scores from viewers and critics. In addition, pre-release aggregate data from focus group testing may be helpful for refining content and marketing plans prior to release. After a film is released, aggregated scores based on pre-release test screenings may be published to promote the work. Thus, biometric measurement of emotional response is not only useful to measure subconscious audience engagement with cinematic (or gaming) content, but also to enable comparison of audience engagement power across genre and type. Further illustrative figures and text and presented in the accompanying Appendix, titled "Biometric Movie Ratings."

Figure 9B:
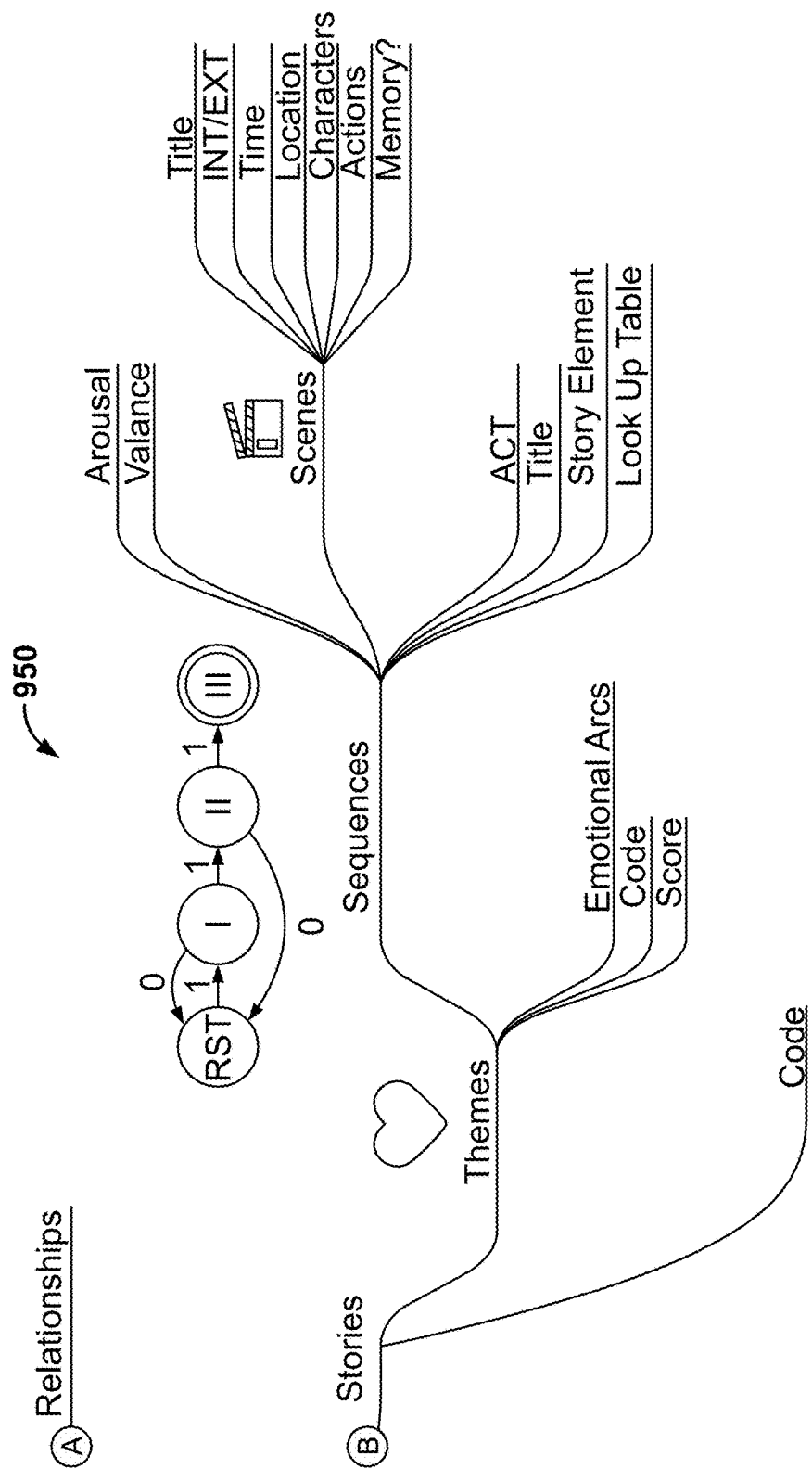

FIG. 10 shows aspects of a real-time scene selection method 1000 in response to a user's (player actor's) emotional state or aggregate of emotional states for multiple users, as may be executed by a processor of a media player, alone or with supporting nodes of a network. The method 1000 is illustrated for immersive mixed reality (MX/R) content but may be adapted for non-immersive content by one of ordinary skill. Input 1010 includes a real-time indicator of a user's emotional state, for example as provided by the process 640 described regarding FIG. 6. Input may further include content navigation data, as mapped and described in connection with FIGS. 7-9. A comparator module or process 1030 processes the inputs 1010, 1020 and determines an error measurement and direction (trend) 1040 of the user's emotional state and trajectory relative to a targeted emotional arc. The error measurement and related data 1040 may be provided to the process 630 for AI training and prediction and also to a selection process 1050 that may select compensatory scenes and objects to correct for the error. Output of the selector 1050 may include identifiers for selected scene and supporting objects 1060. The identifiers 1060 may be provided to a compiler/rendering process 1070 that calls the scene and supporting object data from the cinematic content data structure using the identifiers 1060. The compiler/renderer 1070 outputs mixed reality data 1080 (or other audio/video data) that is output 1090 by an output device, for example, by a mixed reality headset or flat screen display device.

FIG. 11 show a selection algorithm method 1100 for real-time scene or object selection in response to a user's emotional state, such as may be used by the selector process 1050 diagrammed in FIG. 10. At 1110, a processor receives error data indicating a difference between a user's emotional state and a targeted state defined by an emotional arc for the content. Two different approaches are diagrammed. In a first approach, the processor predicts, at 1120, corrective stimuli for the error using a machine learning algorithm. At 1130, the processor matches the most likely corrective stimuli to available scene nodes and supportive objects. Available scene nodes and objects are those downstream of the current scene in the cinematic content map. The processor identifies combinations of downstream objects in the cinematic content DAG (the "story network") that match the tempo, tone, and timing of the desired stimulus. At 1140, the processor selects the closest allowable combination and outputs 1180 the result to a downstream process.

In a second approach, at 1150 the processor identifies predetermined emotional profiles of downstream nodes in the story network and of the player actor. The processor scores 1160 the nodes based on comparing the node and player actor profiles relative to the error information. At 1170, the processor selects the highest scoring allowable combination of downstream nodes, and at 1180 outputs the selected combination to a downstream process.

Figure 12:
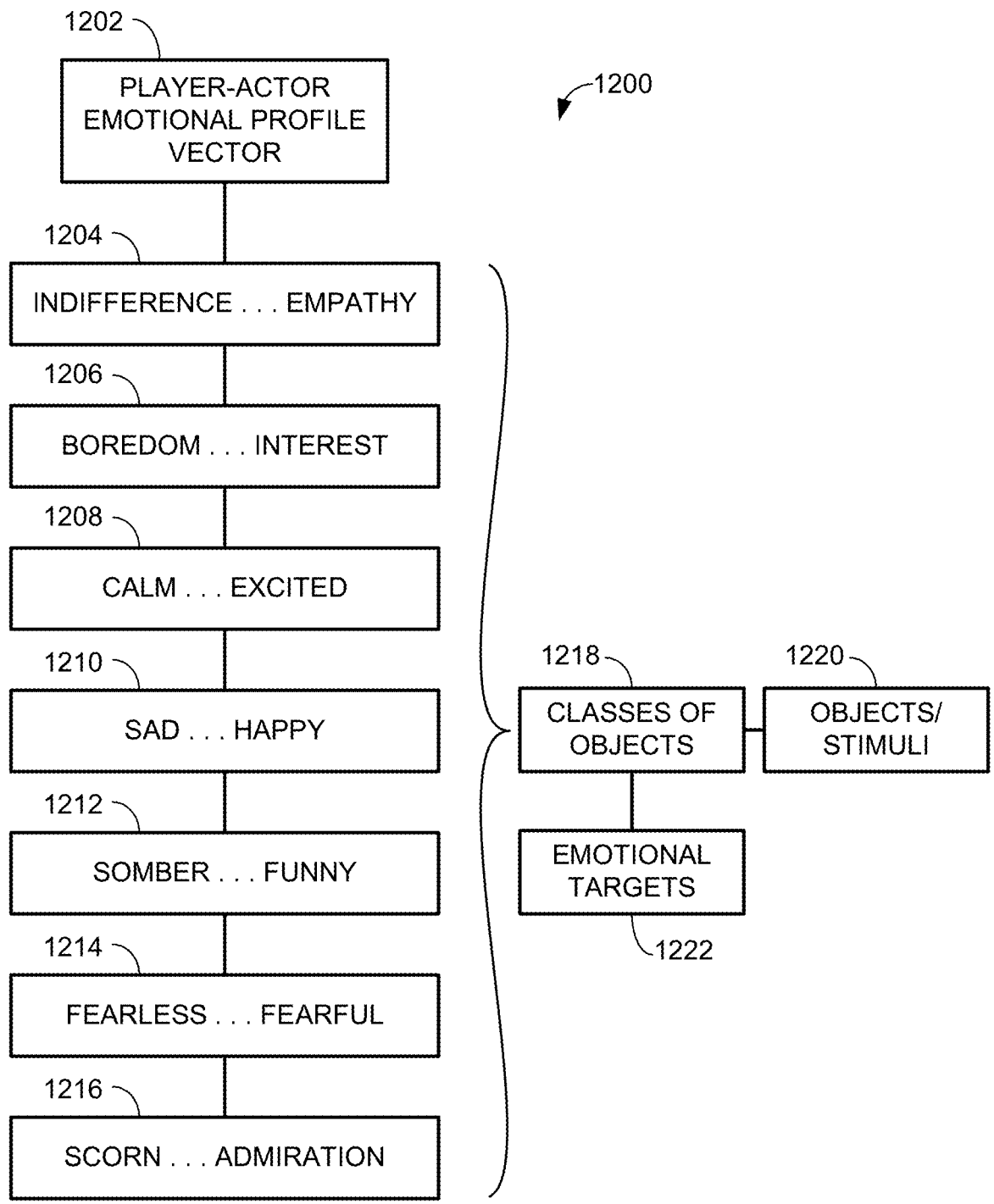
FIG. 12 is a block diagram illustrating aspects of emotional profile vectors as may be used for real-time scene or object selection in response to a user's emotional state.

FIG. 12 shows an example of an emotional profile vector 1200 as may be used for real-time scene or object selection in response to a user's emotional state. A scaled data structure 1202 may include bipolar pairs of emotional qualities between which a numeric scale can extend. Examples of bipolar pairs include indifference/empathy 1204, boredom/interest 1206, calm/excited 1208, sad/happy 1210, somber/funny 1212, fearless/fearful 1214, and scorn/admiration 1216. The bipolar pairs represent a vector, in which each pair has a place in the vector indicating a value in the emotional spectrum between the opposite terminals of the pair. The emotional scale or vector 1202 can describe classes of objects 1218, objects/stimuli 1220, or emotional targets 1222 defined by an emotional arc. Valence is an example of a general emotional profile between positive and negative emotion, and may be refined by sensor data to indicate a category of emotions per the examples above. As used herein, an emotional profile is measure of valence divided into one or more categories.

Figure 13:
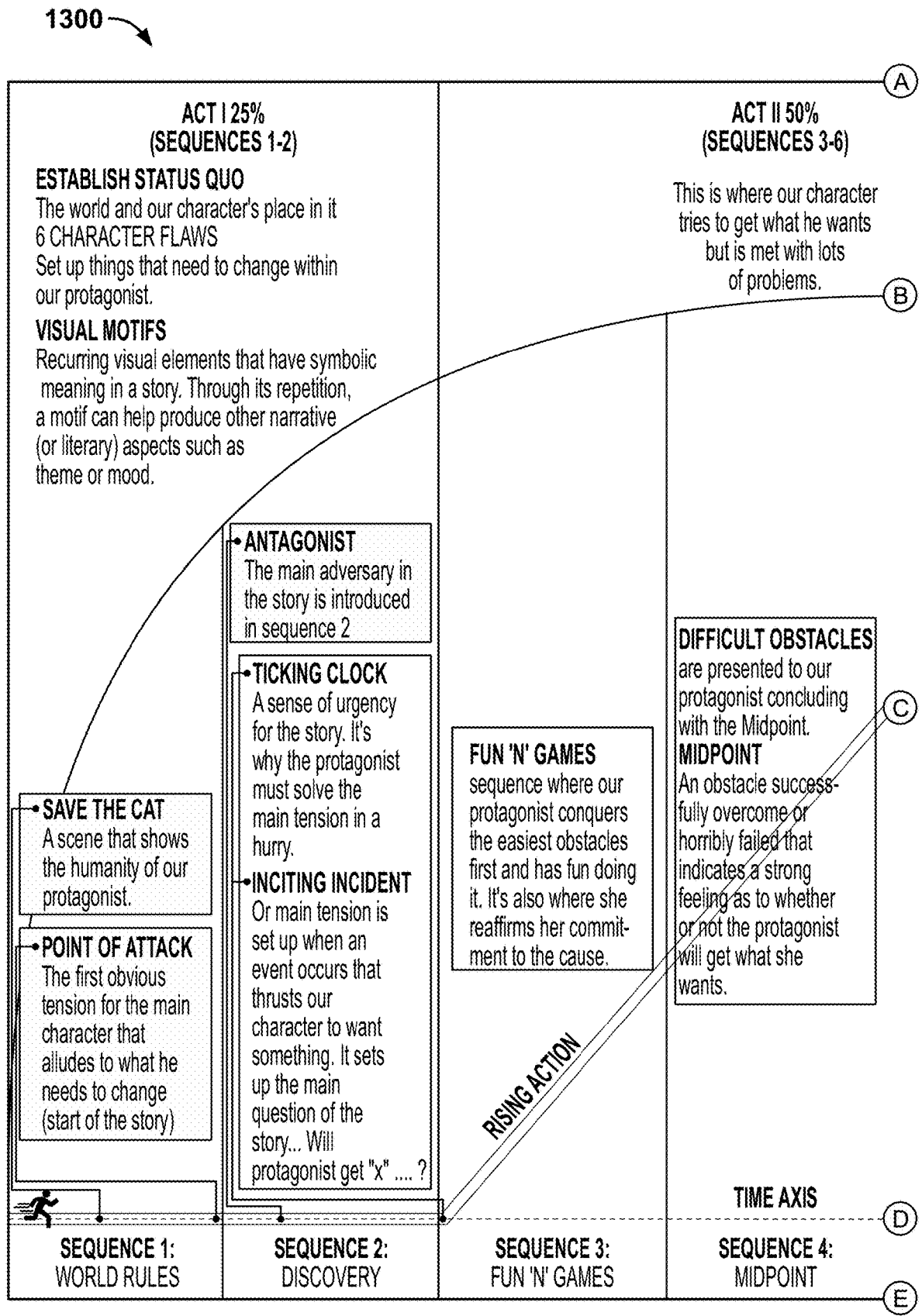
FIG. 13 is a concept diagram illustrating an example of semantic elements for a story in a three-act emotional arc.
Figure 13:
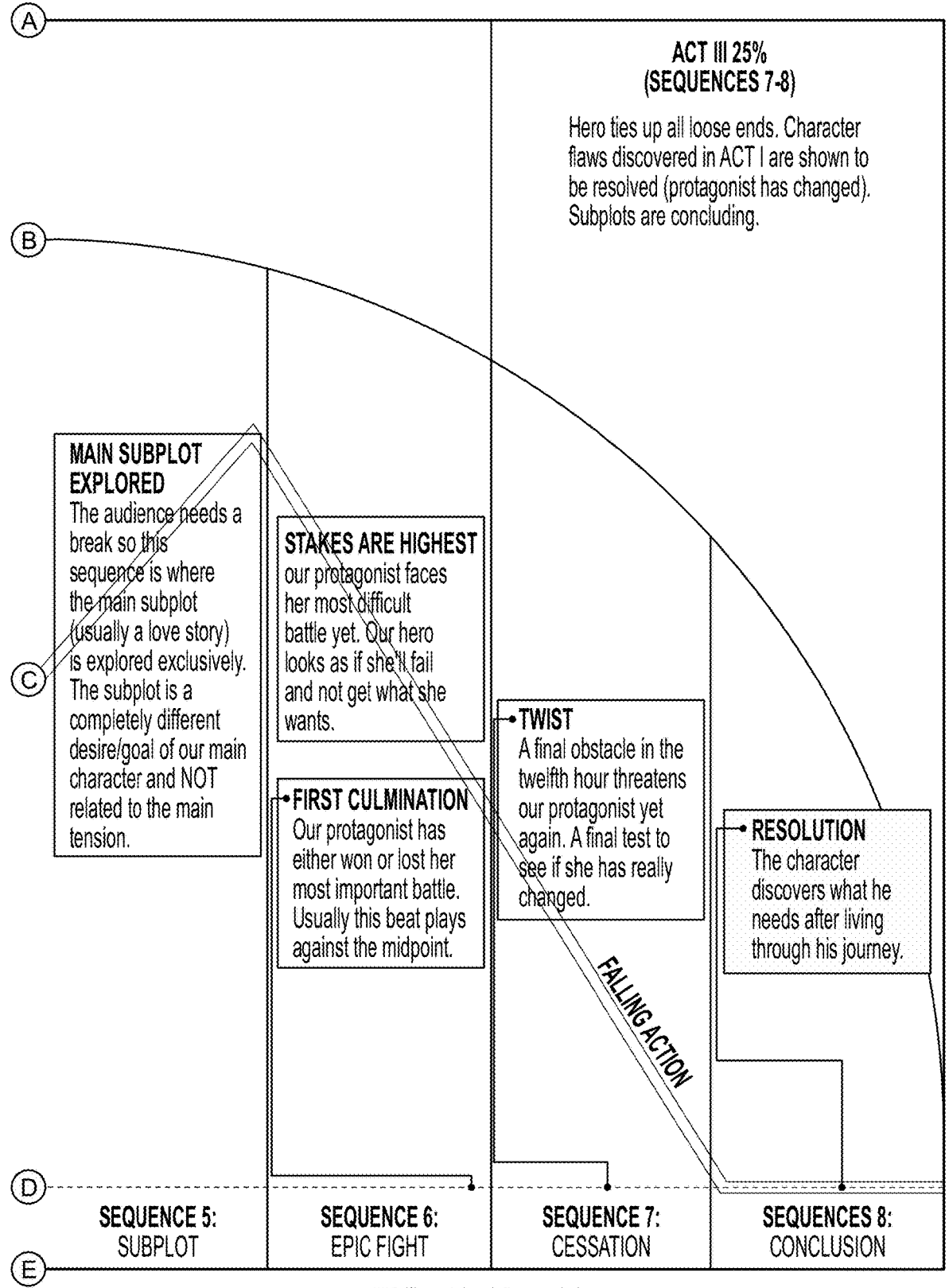

FIG. 13 shows a more detailed example of a three-act emotional arc 1300 with human-readable narrative commentary. The correlation to a timeline is apparent. Accordingly, the arc 13 can fit into a map for cinematic content as shown in FIG. 8. A machine-readable arc would not need human commentary and should include more detailed emotional information that relates to biometric sentic modulation data in a quantitative way, such as by using an emotional profile vector as described above. Nonetheless, the arc 1300 is useful for showing origins of a machine-readable emotional arc in human-perceivable narrative structure and illustrates a well-known three-act structure.

Figure 14:
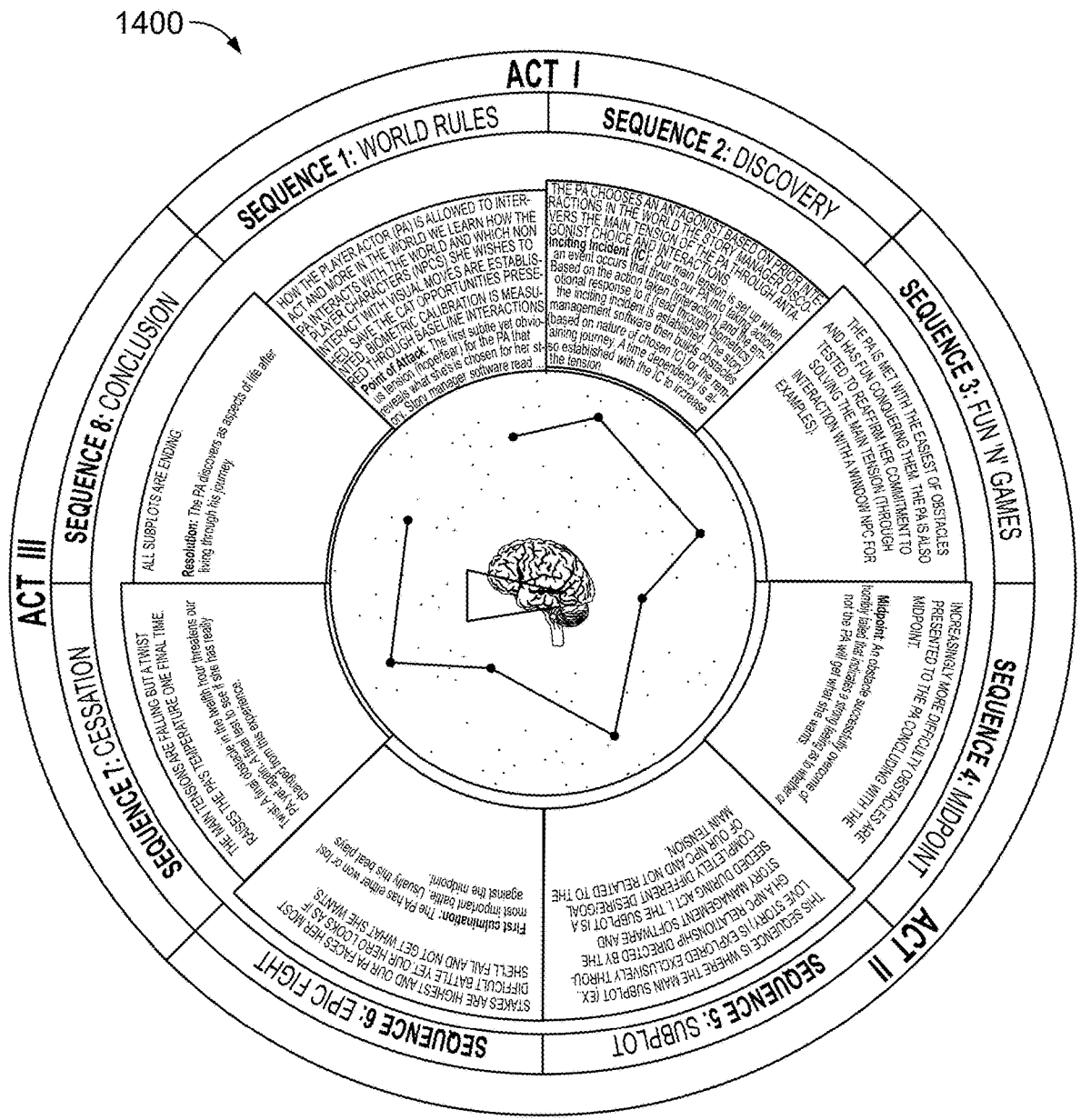
FIG. 14 is a concept diagram illustrating examples of interactions between a player actor and system or method controlling output of digital cinematic content responsive to sensor data indicating a user's emotional state with reference to a predetermined emotional arc.

FIG. 14 shows examples of interactions 1400 between a player actor and system or method controlling output of digital cinematic content responsive to sensor data indicating a user's emotional state with reference to a predetermined emotional arc. In narrative theory, the curves and sequence emotions presented in FIGS. 13-14 provide examples of what has been observed to be the most popular types of stories and their associated emotional responses. There are less popular (at least in the US) structures that appeal to the intellect over emotions. For these narrative structures, cinematic content may be configured to respond to other biometric signals. For example, in lieu of finding emotion, sensors may be used to measure cognitive workload to determine ("test") when a person is cognitively engaged and aroused, to which the cinematic content will be is configured to respond. For people who display their emotions less than most, a key factor is valence that may be harder to measure. But arousal can still be measured even for non-demonstrative types using sensors that do not rely on visible emotional indicators, so the model may adapt and look for cognitive work load and arousal. A media player may include, for example, a system of sensors trained to monitor the biological (sentic modulation) for engagement against the targeted emotional arc. The targeted arc can include both emotional and cognitive (intellectual engagement) components.

A cognitive AI process tests for two things: (1) Interaction success—has the NPC AI convinced the player actor to do what they wish i.e has the NPC AI achieved their goal; and (2) Biometric Data—A "tell" on how the player actor feels about this interaction, i.e., are they engaged (this is the value for entertainment value in narrative theory). Overall engagement throughout the experience is monitored and scored upon completion of the experience. Overall user enjoyment is measured as the difference between expectation biometric data modulation power (as measured during calibration) and the average sustained biometric data modulation power.

The biometric data acts as a three-dimensional vector which provides cognitive workload, arousal and valence from which a processor can determine primary and secondary emotions after calibration. The user's mood going into the interaction affects how the "story" is interpreted so the story experience should try to calibrate it out if possible. If a process is unable to calibrate out mood, then it may take it into account in the emotional arcs presented to favor interactions correlated with higher valence, provided the story controller is receiving biometric data indicating a measure of the player actor's valence state. The instant system and methods will work best for healthy and calm individuals though it will present an interactive experience for everyone who participates.

Figure 15A:
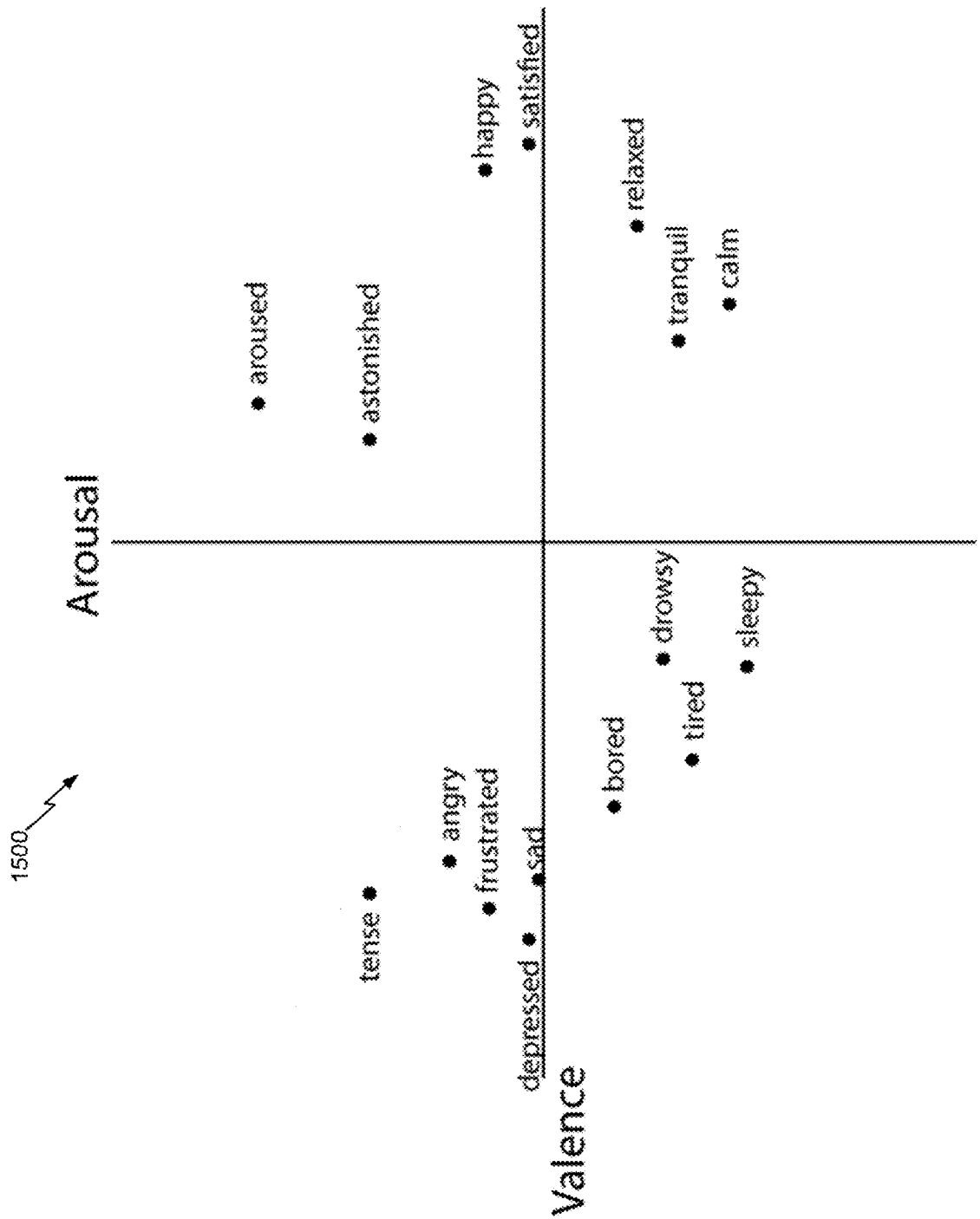
FIG. 15A is a diagram indicating an arrangement of emotional states relative to axes of a two-dimensional emotional space.

FIG. 15A shows an arrangement 1500 of emotional states relative to axes of a two-dimensional emotional space. If the player actor strays, then the system may "test" them by introducing new characters that are meant to elicit an emotional response. The character that is successful then establishes the new path and the emotional arc of that storyline is executed considering the previous path.

Relevant emotions based on a valence/arousal emotional model are shown in the arrangement 1500. A media player client may measure valence with biometric sensors that measure facial action units, while arousal measurements may be done via GSR measurements for example. Possible valence/arousal sequence targets per story element could be the following:

Sequence 1: Negative valence with above baseline sustained arousal following an interaction from goal-oriented object, situation or NPC AI (point of attack test objects).

Sequence 2: Negative valence with way above baseline sustained arousal following an interaction from goal-oriented object, situation or NPC AI (inciting incident test objects).

Sequence 3: Positive valence with above baseline sustained arousal following an interaction from goal-oriented object, situation or NPC AI (fun & games test objects—rising action).

Sequence 4: Positive valence with way above baseline sustained arousal following an interaction from goal-oriented object, situation or NPC AI (Midpoint) followed by a strong and abrupt reversal in valence in the opposing direction.

Sequence 5: Negative valence slowly increasing toward positive, decreasing arousal following an interaction from goal-oriented object, situation or NPC AI (subplot test objects . . . return of character from previous encounter from ACT I).

Sequence 6: Neutral valence slowly decreasing negative, with increasing arousal following an interaction from goal-oriented object, situation or NPC AI (Epic fight test objects).

Sequence 7: Valence neutralizes, and arousal stabilizes. Twist objects "test" for increased arousal and negative valence one last time (twist fight test objects).

Sequence 8: Positive valence and baseline arousal.

Figure 15B:
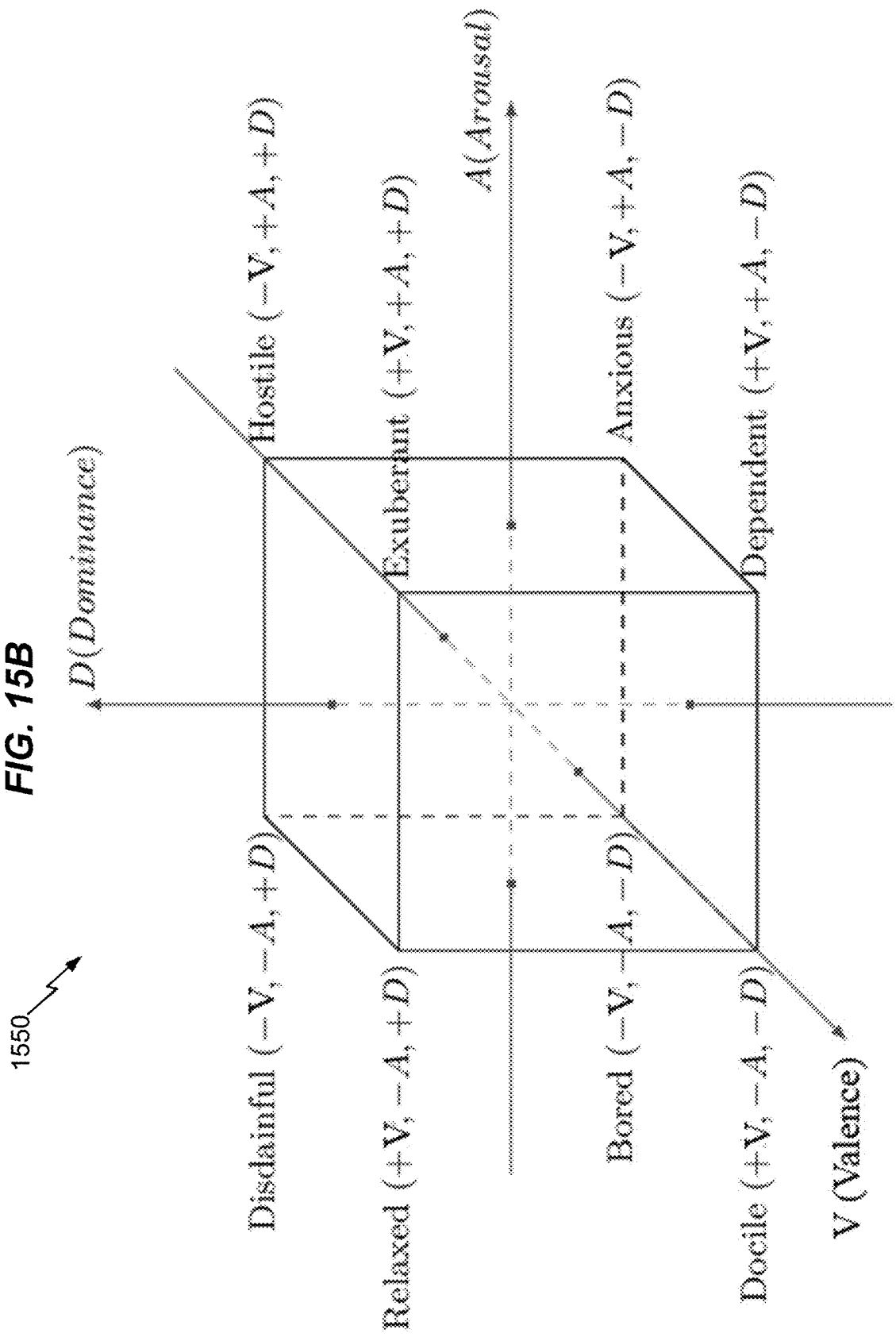
FIG. 15B is a diagram indicating an arrangement of emotional states relative to axes of a three-dimensional emotional space.

Emotional spaces may be characterized by more than two axes. FIG. 15B diagrams a three-dimensional model 1550 of an emotional space, wherein the third axis is social dominance or confidence. The model 1550 illustrates a VAD (valence, arousal, confidence) model. The 3D model 1550 may be useful for complex emotions where a social hierarchy is involved.

Baseline arousal and valence may be determined on an individual basis during emotion calibration. The above sequences map out emotions experienced on the valence arousal scale. Actual story however is defined by "test" objects that interact with the player actor in hopes of eliciting a target emotion. This is one way the story emerges, but the emotional arc doesn't necessarily have to. If an emotional target is failing, then a processor may change the emotional arc plan to one more suitable for the present player actor or mood. This may include, for example, reviving a character who from previous experience elicits a strong response.

Figure 17:
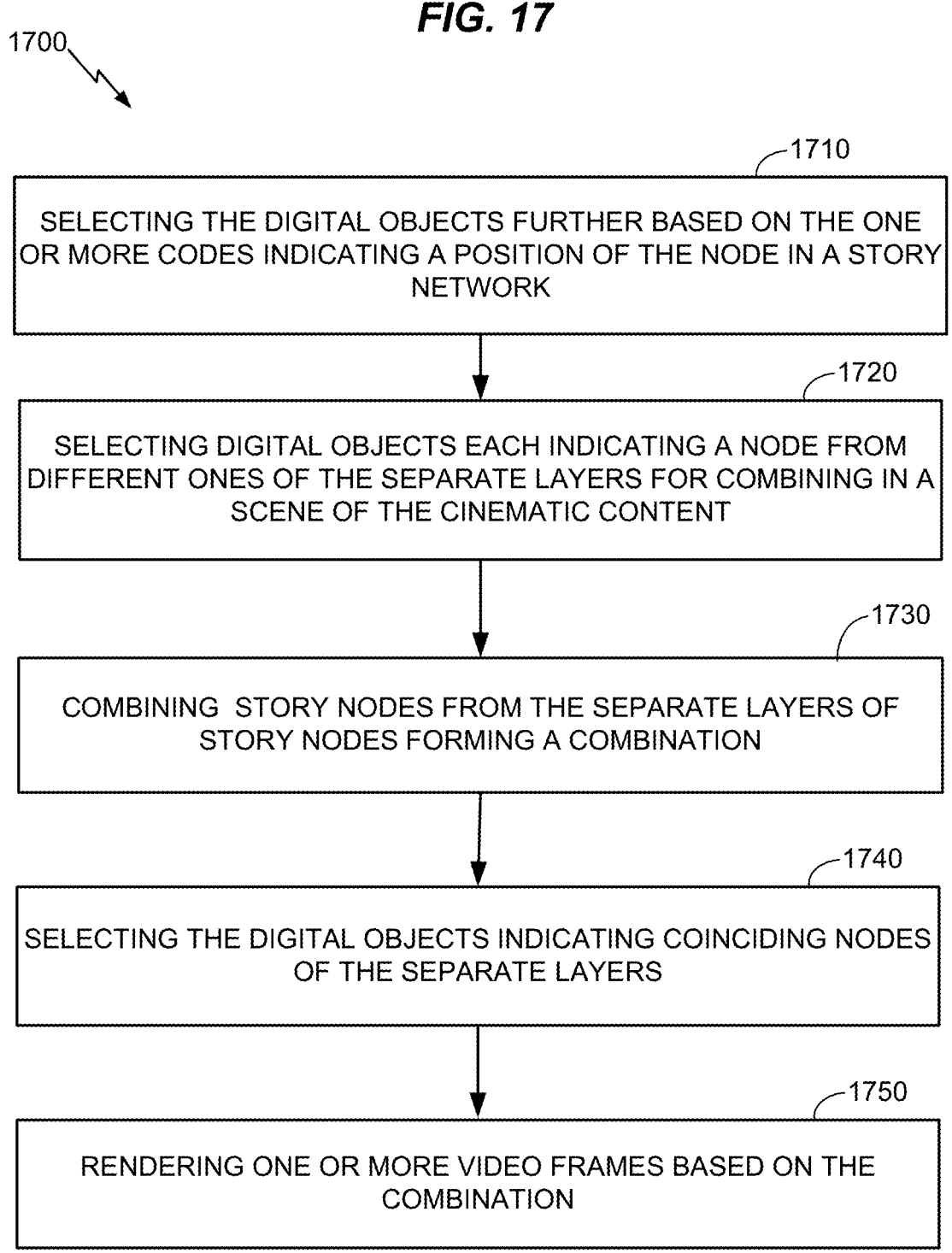
FIGS. 17-18 are flow charts illustrating further optional aspects or operations of the method diagrammed in FIG. 16.
Figure 18:
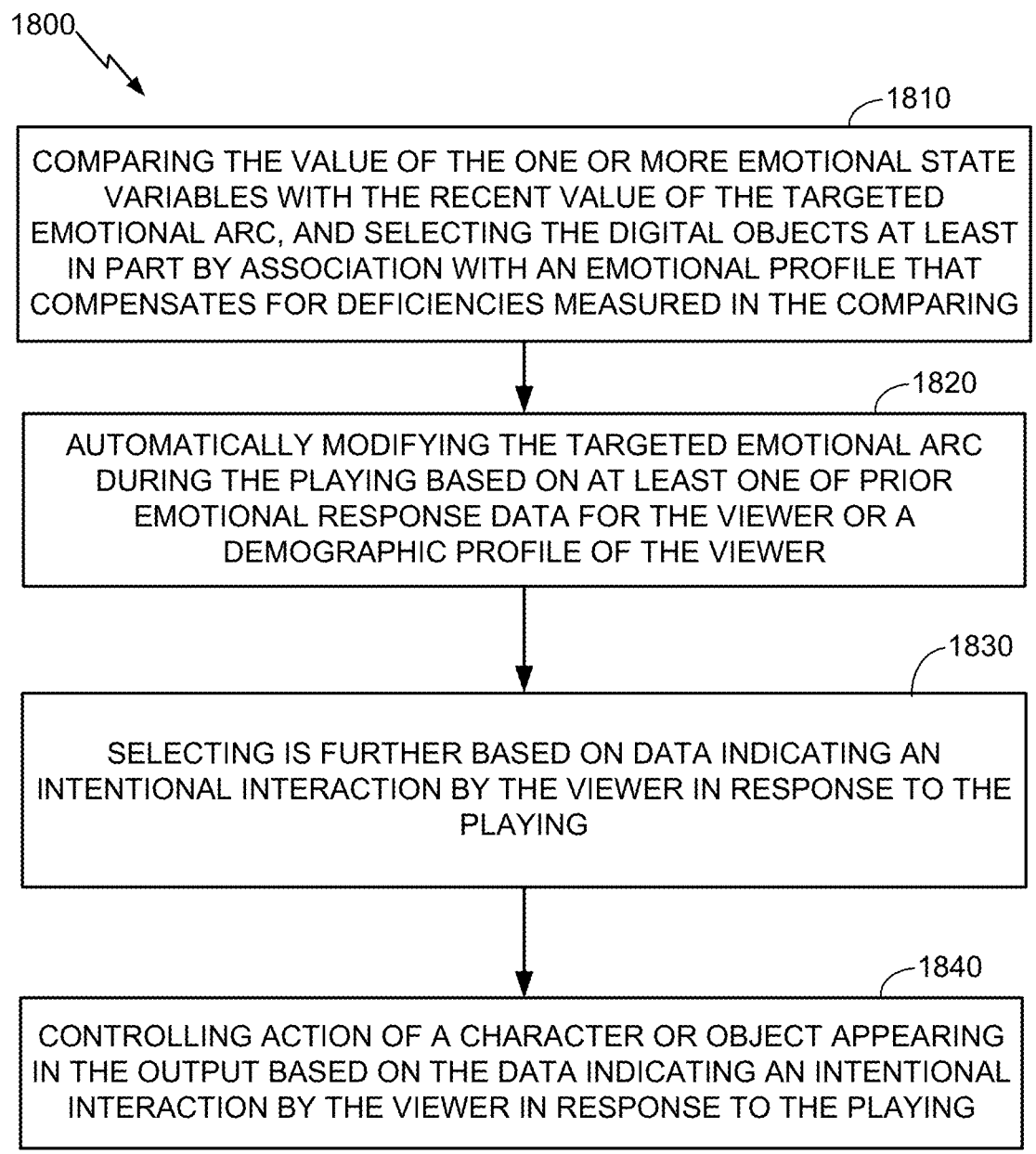

In view the foregoing, and by way of additional example, FIGS. 16-18 show aspects of a method 1600 or methods for controlling output of digital cinematic content responsive to sensor data indicating a user's emotional state. The method 1600 may be performed by an immersive MX/R output device or a non-immersive flat screen device including a programmable computer, by one or more computers in communication with the output device, or by a combination of an output device and one or more computers in communication with the output device.

Referring to FIG. 16, a computer-implemented method for controlling output of digital cinematic content responsive to sensor data indicating a user's emotional state may include, at 1610, accessing, by a processor of the media player, a cinematic content package. The content package includes, or is linked to, a targeted emotional arc as described herein. The emotional arc includes a time sequence (timeline) of encoded binary values each indicating an emotional state for a portion of the arc's timeline. The encoded binary values, also called emotional state variables, are related to biometric sentic modulation data for a user, or for a cohort of users, via an artificial intelligence (machine learning) module. A set of such variables may make up an emotional state vector. As used herein, the term "emotional state variable" encompasses encoded values indicating any variable neurological or neurophysiological state useful for content control, whether or not colloquially considered an "emotion." For example, whether or not curiosity or interest are considered emotions, as neurological states they may be encoded in an emotional state variable. The content package further includes, or is linked to, a collection of digital objects each associated with one or more codes indicating an emotional profile (e.g., impact score) of the each digital object. The digital objects may be of any type described herein above. The one or more codes may be derived using empirical user biometric data processed using AI and are predictive of a likely emotional effect of the digital object for the user or cohort of users.

The method 1600 may include, at 1620, playing digital objects selected from the content package thereby outputting an audio-video signal for display by an output device. The method 1600 may include, at 1630, receiving sensor data from at least one sensor positioned to sense a variable biometric feature of a viewer watching the output device, wherein the variable biometric feature indicates a neurological or neurophysiological state of the viewer. The sensor data may originate from any one or more of various types of biometric sensors as described herein above.

The method 1600 may include, at 1640, determining a value of one or more emotional state variables, based on the sensor data. For example, an AI module receives real-time biometric data from a user viewing the content and selects one or more emotional state variables, based on its training set. The module may assemble the variables into an emotional state vector expressed as a binary number, which the module may provide to a downstream content selection process. The AI module may be trained as described in connection with FIG. 6. An example of an emotional state vector is diagrammed in FIG. 12.

The method 1600 may include, at 1650, the processor selecting the digital objects for the playing based on the value of the one or more emotional state variables, a recent value of the targeted emotional arc, and the one or more codes indicating an emotional profile. Selecting the digital objects may include more detailed operations as described in connection with FIG. 11, and elsewhere herein.

The method 1600 may include any one or more of additional operations 1700 or 1800, shown in FIGS. 17-18, in any operable order. Each of these additional operations is not necessarily performed in every embodiment of the method, and the presence of any one of the operations 1700 or 1800 does not necessarily require that any other of these additional operations also be performed.

Referring to FIG. 17 showing certain additional operations 1700 for navigating a story network, the method 1600 may further include, at 1710, selecting the digital objects further based on the one or more codes indicating a position of the node in a story network. Each of the digital objects may be encoded with one or more codes indicating a node of a story network. The story network may be made up of a directed acyclic graph (DAG) of scenes, as described in connection with FIG. 8. The selecting may include eliminating nodes that are not downstream of a current node, thereby obtaining available nodes. The selecting may further include identifying a combination of the available nodes having an aggregate emotional influence that scores highest for influencing a user to a targeted emotional state.

In an aspect, the story network includes a set of nodes including the selected node. Each of the nodes except for first and last ones of the nodes may be uniquely associated with one or more acceptable antecedent nodes consisting of a first proper non-empty subset of the set of nodes, and with one or more acceptable subsequent nodes consisting of a second proper non-empty subset of the set of nodes excluding the first proper non-empty subset. The antecedent nodes and subsequent nodes of each of the nodes may indicate its position in the story network.

The story network may include various layers of digital objects, for example as shown in FIG. 8, 9A or 9B. In a related aspect, the method 1600 may include, at 1720, selecting digital objects each indicating a node from different ones of the separate layers for combining in a scene of the cinematic content. In a related aspect, the method 1600 may include, at 1730, combining story nodes from the separate layers of story nodes forming a combination. The combination may be identified by having an aggregate emotional influence that scores highest for influencing a user to a targeted emotional state, for example, using a deep neural network or other machine learning algorithm. The method may include combining the digital objects to produce scene data, and providing the scene to a user output device.

The method 1600 may include, at 1740, selecting the digital objects indicating coinciding nodes of the separate layers. As used herein, a "coinciding node" is a digital object that is linked by a data record or other association to another digital object. For example, a non-player character node may be linked to one or more scenes, a set of character scripts, and a set of props or accessories. Examples of coinciding nodes are shown in FIG. 8.

In addition, the method 1600 may include, at 1750, rendering one or more video frames based on the combination of video objects.

Referring to FIG. 18 showing certain additional operations 1800, the method 1600 may further include, at 1810, the processor comparing the value of the one or more emotional state variables with the recent value of the targeted emotional arc and selecting the digital objects at least in part by association with an emotional profile that compensates for deficiencies (error) measured in the comparing. As noted, the targeted emotional arc may include a set of targeted emotional values each uniquely associated with a different interval of a continuous time sequence. The method 1600 may further include, at 1820, automatically modifying the targeted emotional arc during the playing based on at least one of prior emotional response data for the viewer or a demographic profile of the viewer. Modifying may include, for example, removing content that the player actor's sensed emotions or the content's known emotional profile indicates is, or is likely to be, offensive or off-putting. For instance, if the NPC with whom a user is interacting would usually be snarky and mention some sensitive political issues or religious issues, then for a user who is upset and put off by such language, gestures, or behavior, the method may include omitting the sensitive content, and optionally substituting content that the user is more likely to find non-offensive. If the story software is well designed, the effect is not mere censorship, but rather achieving the director's dramatic purpose by avoiding emotional triggers that work against that purpose. Conversely, the method may include introducing edgy content that would otherwise not appear for users whose emotional profile indicates that the edgier-than-normal content will better achieve the targeted emotional arc in those viewers. For example, some users may associate edgy dialog or actions with a relatable hero; for others, the same conduct may cause the player actor to perceive the source as villainous or unsympathetic.

Emotional responses detected by biometric sensors are usually unintentional. In addition, the method 1600 may further include, at 1830, performing the selecting further based on data indicating an intentional interaction by the viewer in response to the playing. The cinematic content may support interactive objects such as non-player characters described herein above, or other interactive objects. The user's interaction with these objects provides emotional state information for the content navigation process and may also influence the user towards an emotional state targeted by the content's emotional arc. Accordingly, the method 1600 may further include, at 1840, controlling action of a character or object appearing in the output based on the data indicating an intentional interaction by the viewer in response to the playing of the digital objects selected from the content package and in response to user input indicating the intentional interaction. The intentional interaction may include, for example, one or more of: speech directed to a character appearing in the output, an intentional muscle movement sensed by a user interface device or sensor, or intentional brain activity sensed by an electrical sensor. The method may include controlling, by the processor, action of a character or object appearing in the output based on the data indicating an intentional interaction by the user in response to the playing.

People are complicated, and sometimes profess one view or position while suppressing their feelings about the issue. In other words, people can have internal conflicts, sometimes about issues that involve social relations. Thus, operations story software may sometimes reveal conflicts between what a user professes to like or dislike, and what their emotional tells reveal. In some cases, the revealing of internal conflicts may be embarrassing for the user or create other negative social reactions. For example, some viewers may have a positive limbic reaction to nudity but may find such responses uncomfortable or embarrassing, depending on the viewing circumstances. Accordingly, in an aspect of the method, the control processor may provide the user with the option of ignoring the user's biometric emotional indicators in favor of some default content calculated to be non-controversial for the user profile. For example, the story controller may receive an intentional or unintentional input such as, for example, through a control interface to alert it that the content is socially or personally undesirable for the user. The controller may accumulate the intentional input over time to refine viewer's emotional profile so that the content stimulates the user's emotions within the limits of the user's higher-level functions (e.g., intellectual and social) to facilitate user comfort. In addition, or in the alternative, the cinematic AI might be calibrated before each viewing experience by intentional input during a trailer or prelude. Using a control interface, the AI may gather information to better accommodate the user's short-term and long-term internal conflicts at play for the viewing experience at hand.

Figure 19:
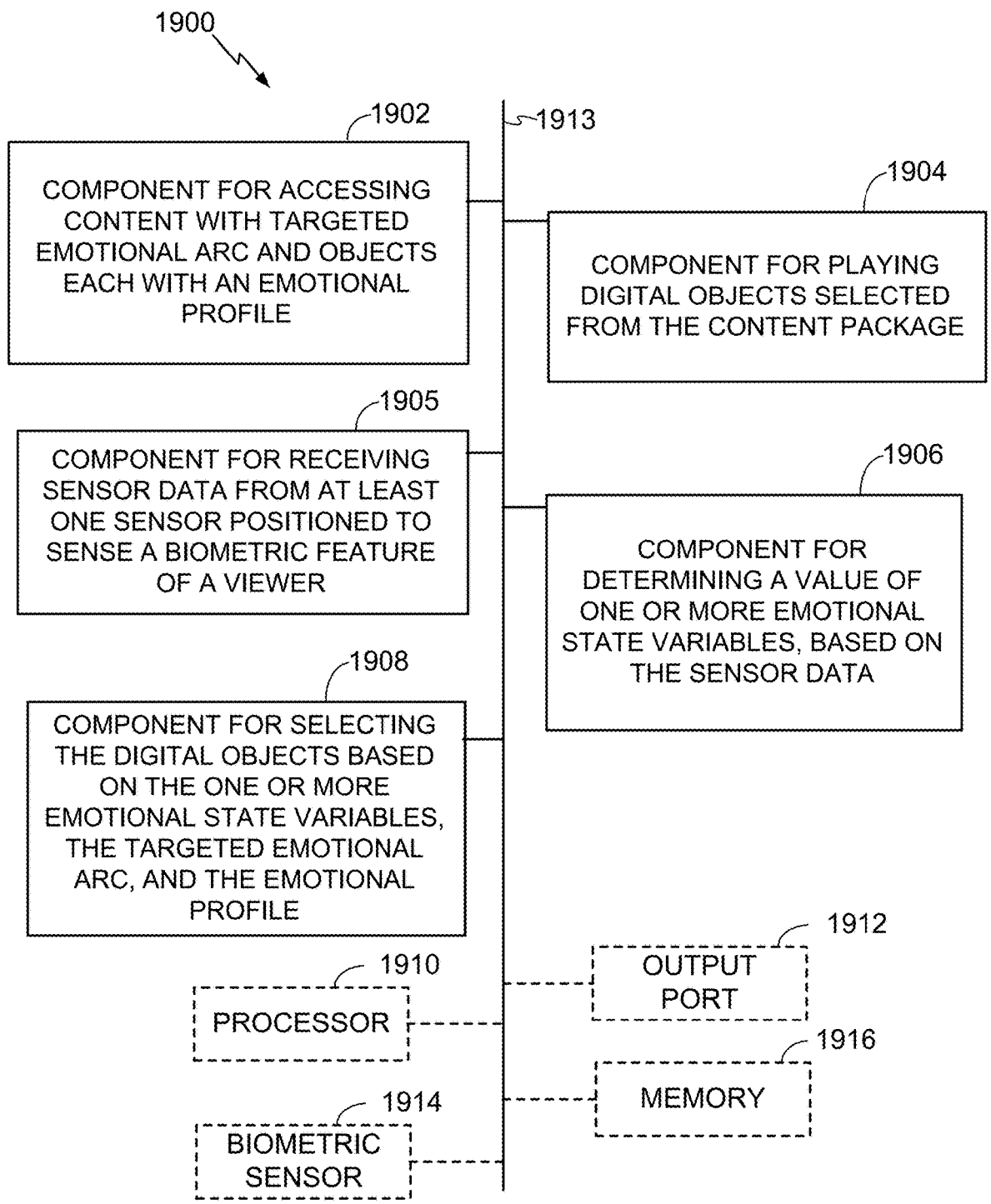
FIG. 19 is a conceptual block diagram illustrating components of an apparatus or system for controlling output of digital cinematic content responsive to sensor data indicating a user's emotional state.

FIG. 19 is a conceptual block diagram illustrating components of an apparatus or system 1900 for controlling output of digital cinematic content responsive to sensor data indicating a user's emotional state. The apparatus or system 1900 may include additional or more detailed components for performing functions or process operations as described herein. For example, the processor 1910 and memory 1916 may contain an instantiation of a process for navigating a story network in response to sentic modulation data as described herein above. As depicted, the apparatus or system 1900 may include functional blocks that can represent functions implemented by a processor, software, or combination thereof (e.g., firmware).

As illustrated in FIG. 19, the apparatus or system 1900 may comprise an electrical component 1902 for accessing content with a targeted emotional arc and objects each with an emotional profile. The component 1902 may be, or may include, a means for said accessing. Said means may include the processor 1910 coupled to the memory 1916, and to an output of a sensor array (not shown), the processor executing an algorithm based on program instructions stored in the memory. Such algorithm may include a sequence of more detailed operations, for example, receiving an encoded digital data package containing the content with arc and objects, or a link to the same; executing an application including a routine configured for reading the digital data package; reading the digital data package by the executing application, and loading the emotional arc and one or more of the objects into short-term memory (e.g., random-access memory) coupled to the processor.

The apparatus 1900 may further include an electrical component 1904 for playing digital objects selected from the content package. The component 1904 may be, or may include, a means for said playing. Said means may include the processor 1910 coupled to the memory 1916, the processor executing an algorithm based on program instructions stored in the memory. Such algorithm may include a sequence of more detailed operations, for example, determining a current digital object or set of digital objects for playing, rendering or obtaining the current digital object or set of digital objects thereby producing digital audio-video data, and outputting the audio-video data to any suitable output device.

The apparatus 1900 may further include an electrical component 1905 for receiving sensor data from at least one sensor positioned to sense a variable biometric feature of a viewer indicate of a neurological or neurophysiological state. The component 1905 may be, or may include, a means for said receiving. Said means may include the processor 1910 coupled to the memory 1916 and to one or more biometric sensors 1914, the processor executing an algorithm based on program instructions stored in the memory. Such algorithm may include a sequence of more detailed operations, for example, receiving data at one or more input ports, each associated with a sensor; converting the data to digital form if received in analog form; processing the data thereby deriving a more compact representation of information it contains; tagging and timestamping the more compact representation with source-identifying information, providing the tagged and timestamped data to a downstream process or saving it to a designated memory location or data structure.

The apparatus 1900 may further include an electrical component 1906 for determining a value of one or more emotional state variables, based on the sensor data. The component 1906 may be, or may include, a means for said determining. Said means may include the processor 1910 coupled to the memory 1916, the processor executing an algorithm based on program instructions stored in the memory. Such algorithm may include a sequence of more detailed operations, for example, as described in connection with FIG. 6.

The apparatus 1900 may further include an electrical component 1908 for selecting the digital objects based on the one or more emotional state variables, the targeted emotional arc, and the emotional profile. The component 1908 may be, or may include, a means for said selecting. Said means may include the processor 1910 coupled to the memory 1916, the processor executing an algorithm based on program instructions stored in the memory. Such algorithm may include a sequence of more detailed operations, for example, as described in connection with FIGS. 10-11.

The apparatus 1900 may optionally include a processor module 1910 having at least one processor. The processor 1910 may be in operative communication with the modules 1902-1908 via a bus 1913 or similar communication coupling. In the alternative, one or more of the modules may be instantiated as functional modules in a memory of the processor. The processor 1910 may effect initiation and scheduling of the processes or functions performed by electrical components 1902-1908.

In related aspects, the apparatus 1900 may include a network interface module (not shown) operable for communicating with system components over a computer network. A network interface module may be, or may include, for example, an Ethernet port or serial port (e.g., a Universal Serial Bus (USB) port), a Wifi interface, or a cellular telephone interface. In further related aspects, the apparatus 1900 may optionally include a module for storing information, such as, for example, a memory device 1916. The computer readable medium or the memory module 1916 may be operatively coupled to the other components of the apparatus 1900 via the bus 1913 or the like. The memory module 1916 may be adapted to store computer readable instructions and data for effecting the processes and behavior of the modules 1902-1908, and subcomponents thereof, or the processor 1910, the method 1600 and one or more of the additional operations 1700-1800 disclosed herein, or any method for performance by a media player described herein. The memory module 1916 may retain instructions for executing functions associated with the modules 1902-1908. While shown as being external to the memory 1916, it is to be understood that the modules 1902-1908 can exist within the memory 1916 or an on-chip memory of the processor 1910.

The memory module 1916 may hold a copy of, or a representation of, the story network comprising a set of nodes including the node, wherein each of the nodes except for first and last ones of the nodes is uniquely associated with one or more acceptable antecedent nodes consisting of a first proper non-empty subset of the set of nodes, and with one or more acceptable subsequent nodes consisting of a second proper non-empty subset of the set of nodes excluding the first proper non-empty subset. In an aspect, the antecedent nodes and subsequent nodes of each of the nodes indicate its position in the story network. In addition, the memory module 1916 may hold a representation of the story network comprising separate layers of story nodes. In such embodiments, the memory 1916 may hold further instructions for selecting digital objects each indicating a node from different ones of the separate layers for combining in a scene of the cinematic content; for performing the playing including combining story nodes from the separate layers of story nodes forming a combination; for performing the selecting at least in part by selecting the digital objects indicating coinciding nodes of the separate layers. In the stored structure of the story network, at least some of the set of nodes may be associated with one or more coinciding nodes in different ones of the separate layers. Further details of the story network and its use in the apparatus may be as described in connection with the Figures herein above.

The apparatus 1900 may include a transceiver 1912 configured as a wireless transmitter/receiver, or a wired transmitter/receiver, for transmitting and receiving a communication signal to/from another system component such as, for example, an RFID tag or location information transmitter. In alternative embodiments, the processor 1910 may include networked microprocessors from devices operating over a computer network. In addition, the apparatus 1900 may include a stereoscopic display or other immersive display device for displaying immersive content, or other suitable output device. A stereoscopic display device may be, or may include, any suitable stereoscopic AR or VR output device as described herein above, or as otherwise known in the art. The apparatus 1900 may include, or may be connected to, one or more biometric sensors 1914, which may be of any suitable types. Various examples of suitable biometric sensors are described herein above.

Those of skill would further appreciate that the various illustrative logical blocks, modules, circuits, and algorithm steps described in connection with the aspects disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

As used in this application, the terms "component", "module", "system", and the like are intended to refer to a computer-related entity, either hardware, a combination of hardware and software, software, or software in execution. For example, a component or a module may be, but are not limited to being, a process running on a processor, a processor, an object, an executable, a thread of execution, a program, and/or a computer. By way of illustration, both an application running on a server and the server can be a component or a module. One or more components or modules may reside within a process and/or thread of execution and a component or module may be localized on one computer and/or distributed between two or more computers.

Various aspects will be presented in terms of systems that may include a number of components, modules, and the like. It is to be understood and appreciated that the various systems may include additional components, modules, etc. and/or may not include all of the components, modules, etc. discussed in connection with the figures. A combination of these approaches may also be used. The various aspects disclosed herein can be performed on electrical devices including devices that utilize touch screen display technologies, heads-up user interfaces, wearable interfaces, and/or mouse-and-keyboard type interfaces. Examples of such devices include VR output devices (e.g., VR headsets), AR output devices (e.g., AR headsets), computers (desktop and mobile), televisions, digital projectors, smart phones, personal digital assistants (PDAs), and other electronic devices both wired and wireless.

In addition, the various illustrative logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device (PLD) or complex PLD (CPLD), discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Operational aspects disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, digital versatile disk (DVD), Blu-Ray™, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a client device or server. In the alternative, the processor and the storage medium may reside as discrete components in a client device or server.

Furthermore, the one or more versions may be implemented as a method, apparatus, or article of manufacture using standard programming and/or engineering techniques to produce software, firmware, hardware, or any combination thereof to control a computer to implement the disclosed aspects. Non-transitory computer readable media can include but are not limited to magnetic storage devices (e.g., hard disk, floppy disk, magnetic strips, or other format), optical disks (e.g., compact disk (CD), DVD, Blu-Ray™ or other format), smart cards, and flash memory devices (e.g., card, stick, or other format). Of course, those skilled in the art will recognize many modifications may be made to this configuration without departing from the scope of the disclosed aspects.

The previous description of the disclosed aspects is provided to enable any person skilled in the art to make or use the present disclosure. Various modifications to these aspects will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

In view of the exemplary systems described supra, methodologies that may be implemented in accordance with the disclosed subject matter have been described with reference to several flow diagrams. While for purposes of simplicity of explanation, the methodologies are shown and described as a series of blocks, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methodologies described herein. Additionally, it should be further appreciated that the methodologies disclosed herein are capable of being stored on an article of manufacture to facilitate transporting and transferring such methodologies to computers.

The invention claimed is:

1. A method for providing cinematic content to a user via a computer-controlled media player, the method comprising:
accessing by a processor of the media player a content package including a targeted emotional arc and a collection of digital objects each associated with one or more codes indicating an emotional profile of the each digital object;
playing digital objects selected from the content package thereby outputting an audio-video signal for display by an output device;
receiving sensor data from at least one sensor positioned to sense a biometric feature of a user watching the output device;
determining a value of one or more emotional state variables, based on the sensor data; and
selecting the digital objects for the playing based on the one or more emotional state variables, a recent value of the targeted emotional arc, and the one or more codes indicating an emotional profile, wherein the selecting further comprises comparing the value of the one or more emotional state variables with the recent value of the targeted emotional arc and selecting the digital objects at least in part by association with an emotional profile that compensates for deficiencies measured in the comparing.

2. The method of claim 1, wherein each of the digital objects is further encoded with one or more codes indicating a node of a story network, and wherein the selecting further comprises selecting the digital objects further based on the one or more codes indicating a position of the node in a story network.

3. The method of claim 2, wherein the story network comprises a set of nodes including the node, each of the nodes except for first and last ones of the nodes uniquely associated with one or more acceptable antecedent nodes consisting of a first proper non-empty subset of the set of nodes, and with one or more acceptable subsequent nodes consisting of a second proper non-empty subset of the set of nodes excluding the first proper non-empty subset, wherein the antecedent nodes and subsequent nodes of each of the nodes indicate its position in the story network.

4. The method of claim 1, wherein the targeted emotional arc comprises a set of targeted emotional values each uniquely associated with a different interval of a continuous time sequence.

5. The method of claim 1, further comprising automatically modifying the targeted emotional arc during the playing based on at least one of prior emotional response data for the user or a demographic profile of the user.

6. The method of claim 1, wherein the selecting is further based on data indicating an intentional interaction by the user in response to the playing, wherein the intentional interaction comprises one or more of: speech directed to a character appearing in the output, an intentional muscle movement sensed by a user interface device or sensor, or intentional brain activity sensed by an electrical sensor.

7. The method of claim 6, further comprising controlling action of a character or object appearing in the output based on the data indicating an intentional interaction by the user in response to the playing.

8. An apparatus for providing cinematic content to a user via a computer-controlled media player, comprising a processor coupled to a memory, the memory holding program instructions that when executed by the processor cause the apparatus to perform:
accessing a content package including a targeted emotional arc and a collection of digital objects each associated with one or more codes indicating an emotional profile of the each digital object;
playing digital objects selected from the content package thereby outputting an audio-video signal for display by an output device;
receiving sensor data from at least one sensor positioned to sense a biometric feature of a user watching the output device;
determining a value of one or more emotional state variables, based on the sensor data; and
selecting the digital objects for the playing based on the one or more emotional state variables, a recent value of the targeted emotional arc, and the one or more codes indicating an emotional profile, wherein the memory holds further instructions for the selecting at least in part by comparing the value of the one or more emotional state variables with the recent value of the targeted emotional arc and selecting the digital objects at least in part by association with an emotional profile that compensates for deficiencies measured in the comparing.

9. The apparatus of claim 8, wherein each of the digital objects is further encoded with one or more codes indicating a node of a story network, and wherein the memory holds further program instructions for the selecting the digital objects based on the one or more codes indicating a position of the node in a story network.

10. The apparatus of claim 9, wherein the memory holds a representation of the story network comprising a set of nodes including the node, wherein each of the nodes except for first and last ones of the nodes is uniquely associated with one or more acceptable antecedent nodes consisting of a first proper non-empty subset of the set of nodes, and with one or more acceptable subsequent nodes consisting of a second proper non-empty subset of the set of nodes excluding the first proper non-empty subset, wherein the antecedent nodes and subsequent nodes of each of the nodes indicate its position in the story network.

11. The apparatus of claim 10, wherein the memory holds a representation of the story network comprising separate layers of story nodes, and the selecting further comprises selecting digital objects each indicating a node from different ones of the separate layers for combining in a scene of the cinematic content, the playing further comprises combining story nodes from the separate layers of story nodes forming a combination, the selecting further comprises selecting the digital objects indicating coinciding nodes of the separate layers, and at least some of the set of nodes are associated with one or more coinciding nodes in different ones of the separate layers.

12. The apparatus of claim 11, wherein the memory holds further instructions for the playing at least in part by rendering one or more video frames based on the combination.

13. The apparatus of claim 8, wherein the memory holds further instructions for processing the targeted emotional arc as a set of targeted emotional values each uniquely associated with a different interval of a continuous time sequence.

14. The apparatus of claim 8, wherein the memory holds further instructions for automatically modifying the targeted emotional arc during the playing based on at least one of prior emotional response data for the user or a demographic profile of the user.

15. The apparatus of claim 8, wherein the memory holds further instructions for the selecting at least in part based on data indicating an intentional interaction by the user in response to the playing, wherein the intentional interaction comprises one or more of: speech directed to a character appearing in the output, an intentional muscle movement sensed by a user interface device or sensor, or intentional brain activity sensed by an electrical sensor.

16. The apparatus of claim 15, wherein the memory holds further instructions for controlling action of a character or object appearing in the output based on the data indicating an intentional interaction by the user in response to the playing.

17. A method for providing cinematic content to a user via a computer-controlled media player, the method comprising:
accessing by a processor of the media player a content package including a targeted emotional arc and a collection of digital objects each associated with one or more codes indicating an emotional profile of the each digital object;
playing digital objects selected from the content package thereby outputting an audio-video signal for display by an output device, wherein each of the digital objects is further encoded with one or more codes indicating a node of a story network, and wherein the selecting further comprises selecting the digital objects further based on the one or more codes indicating a position of the node in a story network, wherein the story network comprises a set of nodes including the node, each of the nodes except for first and last ones of the nodes uniquely associated with one or more acceptable antecedent nodes consisting of a first proper non-empty subset of the set of nodes, and with one or more acceptable subsequent nodes consisting of a second proper non-empty subset of the set of nodes excluding the first proper non-empty subset, wherein the antecedent nodes and subsequent nodes of each of the nodes indicate its position in the story network;
receiving sensor data from at least one sensor positioned to sense a biometric feature of a user watching the output device;
determining a value of one or more emotional state variables, based on the sensor data; and
selecting the digital objects for the playing based on the one or more emotional state variables, a recent value of the targeted emotional arc, and the one or more codes indicating an emotional profile.

18. The method of claim 17, wherein the story network comprises separate layers of story nodes, and the selecting further comprises selecting digital objects each indicating a node from different ones of the separate layers for combining in a scene of the cinematic content, the playing further comprises combining story nodes from the separate layers of story nodes forming a combination, the selecting further comprises selecting the digital objects indicating coinciding nodes of the separate layers, and at least some of the set of nodes are associated with one or more coinciding nodes in different ones of the separate layers.

19. The method of claim 18, wherein the playing further comprises rendering one or more video frames based on the combination.

* * * * *